US008828962B2

(12) United States Patent
Zheng et al.

(10) Patent No.: US 8,828,962 B2
(45) Date of Patent: Sep. 9, 2014

(54) SIRNA COMPOSITIONS AND METHODS FOR POTENTLY INHIBITING VIRAL INFECTION

(75) Inventors: Bojian Zheng, Hong Kong (CN); Hongyan Sui, Frederick, MD (US); Yongping Lin, Hong Kong (CN)

(73) Assignee: Xiangxue Group (Hong Kong) Company Limited, Kowloon (CN)

( * ) Notice: Subject to any disclaimer, the term of this patent is extended or adjusted under 35 U.S.C. 154(b) by 339 days.

(21) Appl. No.: 13/323,364

(22) Filed: Dec. 12, 2011

(65) Prior Publication Data
US 2013/0225651 A1    Aug. 29, 2013

Related U.S. Application Data

(62) Division of application No. 12/636,234, filed on Dec. 11, 2009, now Pat. No. 8,664,188.

(60) Provisional application No. 61/121,614, filed on Dec. 11, 2008.

(51) Int. Cl.
*A61K 31/70* (2006.01)
*C07H 21/02* (2006.01)
*C07H 21/04* (2006.01)
*A61K 31/713* (2006.01)
*A61K 31/7105* (2006.01)
*C12N 15/11* (2006.01)
*C12N 15/113* (2010.01)
*C12Q 1/68* (2006.01)

(52) U.S. Cl.
CPC ........... *A61K 31/713* (2013.01); *A61K 31/7105* (2013.01); *C12N 15/111* (2013.01); *C12N 15/113* (2013.01); *C12N 2310/14* (2013.01)
USPC ........ 514/44 A; 435/375; 536/23.1; 536/24.1; 536/24.5

(58) Field of Classification Search
None
See application file for complete search history.

(56) References Cited

U.S. PATENT DOCUMENTS

2004/0242518 A1*  12/2004  Chen et al. ...................... 514/44

FOREIGN PATENT DOCUMENTS

| WO | WO-2006-121464 A2 | 11/2006 |
| WO | WO-2007-031322 A1 | 3/2007 |
| WO | WO-2007-056861 A1 | 5/2007 |

OTHER PUBLICATIONS

Horimoto, T. & Kawaoka, Y. Influenza: lessons from past pandemics, warnings from current incidents. *Nat. Rev. Microbiol.* 3, 591-600 (2005).
Yuen, K.Y., et al. Clinical features and rapid viral diagnosis of human disease associated with avian influenza A H5N1 virus. *Lancet* 351, 467-471 (1998).
Beigel, J.H., et al. Avian influenza A (H5N1) infection in humans. *The New England Journal of Medicine* 353, 1374-1385 (2005).
Castle, S.C. Clinical relevance of age-related immune dysfunction. *Clin Infect Dis* 31, 578-585 (2000).
Luscher-Mattli, M. Influenza chemotherapy: a review of the present state of art and of new drugs in development. *Archives of virology* 145, 2233-2248 (2000).
Elbashir, S.M., et al. Duplexes of 21-nucleotide RNAs mediate RNA interference in cultured mammalian cells. *Nature* 411, 494-498 (2001).
Fire, A., et al. Potent and specific genetic interference by double-stranded RNA in Caenorhabditis elegans. *Nature* 391, 806-811 (1998).
Ge, Q., et al. Inhibition of influenza virus production in virus-infected mice by RNA interference. *Proceedings of the National Academy of Sciences of the United States of America* 101, 8676-8681 (2004).
Tompkins, S.M., LO, C.Y., Tumpey, T.M. & Epstein, S.L. Protection against lethal influenza virus challenge by RNA interference in vivo. *Proceedings of the National Academy of Sciences of the United States of America* 101, 8682-8686 (2004).
Ge, Q., et al. RNA interference of influenza virus production by directly targeting mRNA for degradation and indirectly inhibiting all viral RNA transcription. *Proceedings of the National Academy of Sciences of the United States of America* 100, 2718-2723 (2003).
Zhou, H., et al. Effective small interfering RNAs targeting matrix and nucleocapsid protein gene inhibit influenza A virus replication in cells and mice. *Antiviral Research* (2007).
Hui, E.K., Yap, E.M., AN, D.S., Chen, I.S. & Nayak, D.P. Inhibition of influenza virus matrix (M1) protein expression and virus replication by U6 promoter-driven and lentivirus-mediated delivery of siRNA. *J Gen. Virol.* 85, 1877-1884 (2004).
McCown, M., Diamond, M.S. & Pekosz, A. The utility of siRNA transcripts produced by RNA polymerase i in down regulating viral gene expression and replication of negative- and positive-strand RNA viruses. *Virology* 313, 514-524 (2003).
Marques, J.T. & Williams, B.R.G. Activation of the mammalian immune system by siRNAs. *Nat Biotech* 23, 1399-1405 (2005).
Judge, A.D., et al. Sequence-dependent stimulation of the mammalian innate immune response by synthetic siRNA. *Nature biotechnology* 23, 457-462 (2005).

(Continued)

*Primary Examiner* — Sean McGarry
(74) *Attorney, Agent, or Firm* — Saliwanchik, Lloyd & Eisenschenk

(57) ABSTRACT

No antiviral regimen has been consistently successful in treating H5N1 virus infection. We demonstrate that a group of highly effective siRNAs targeting different H5N1 viral genes shares a unique motif, GGAGU/ACUCC. We further demonstrate that the effectiveness of siRNAs containing this motif is not sequence specific. The results suggested that the structure of the unique motif is critical in determining the potency of siRNA-mediated protective effects against viral infection and this potent in vivo protection is associated with early productions of β-defensin and IL-6 induced by the motif. Provided are methods and prophylactic and therapeutic agents useful against other viral infections in addition to the H5N1 influenza virus.

10 Claims, 22 Drawing Sheets

(56) References Cited

OTHER PUBLICATIONS

Hornung, V., et al. Sequence-specific potent induction of IFN-alpha by short interfering RNA in plasmacytoid dendritic cells through TLR7. *Nature medicine* 11, 263-270 (2005).

Zheng, B.J., et al. Delayed antiviral plus immunomodulator treatment still reduces mortality in mice infected by high inoculum of influenza A/H5N1 virus. *Proceedings of the National Academy of Sciences of the United States of America* 105, 8091-8096 (2008).

Bitko, V., Musiyenko, A., Shulyayeva, O. & Barik, S. Inhibition of respiratory viruses by nasally administered siRNA. *Nature medicine* 11, 50-55 (2005).

Li, B.-J., et al. Using siRNA in prophylactic and therapeutic regimens against SARS coronavirus in Rhesus macaque. *Nature medicine* 11, 944-951 (2005).

Schlee, M., Hornung, V. & Hartmann, G. siRNA and isRNA: Two Edges of One Sword. *Mol. Ther.* 14, 463-470 (2006).

Sioud, M. Induction of inflammatory cytokines and interferon responses by double-stranded and single-stranded siRNAs is sequence-dependent and requires endosomal localization. *Journal of Molecular Biology* 348, 1079-1090 (2005).

Imai, Y., et al. Identification of oxidative stress and Toll-like receptor 4 signaling as a key pathway of acute lung injury. *Cell* 133, 235-249 (2008).

Salomon, R., Hoffmann, E. & Webster, R.G. Inhibition of the cytokine response does not protect against lethal H5N1 influenza infection. *Proceedings of the National Academy of Sciences of the United States of America* 104, 12479-12481 (2007).

Bals, R. & Hiemstra, P.S. Innate immunity in the lung: how epithelial cells fight against respiratory pathogens. *Eur. Respir. J* 23, 327-333 (2004).

Nadeau, W.J., Pistole, T.G. & McCormick, B.A. Polymorphonuclear leukocyte migration across model intestinal epithelia enhances *Salmonella typhimurium* killing via the epithelial derived cytokine, IL-6. *Microbes and infection / Institut Pasteur* 4, 1379-1387 (2002).

Meusel, T.R. & Imani, F. Viral induction of inflammatory cytokines in human epithelial cells follows a p38 mitogen-activated protein kinase-dependent but NF-kappa B-independent pathway. *J Immunol.* 171, 3768-3774 (2003).

Monick, M.M., et al. Respiratory syncytial virus up-regulates TLR4 and sensitizes airway epithelial cells to endotoxin. *The Journal of Biological Chemistry* 278, 53035-53044 (2003).

Wick, M.J., Madara, J.L., Fields, B.N. & Normark, S.J. Molecular cross talk between epithelial cells and pathogenic microorganisms. *Cell* 67, 651-659 (1991).

Diamond, G., Legarda, D. & Ryan, L.K. The innate immune response of the respiratory epithelium. *Immunological Reviews* 173, 27-38 (2000).

Dentener, M.A., et al. Production of the acute-phase protein lipopolysaccharide-binding protein by respiratory type II epithelial cells: implications for local defense to bacterial endotoxins. *American Journal of Respiratory Cell and Molecular Biology* 23, 146-153 (2000).

Wang, M., et al. Food markets with live birds as source of avian influenza. *Emerging Infectious Diseases* 12, 1773-1775 (2006).

Shuai, X., Merdan, T., Unger, F., Wittmar, M. & Kissel, T. Novel Biodegradable Ternary Copolymers hy-PEI-g-PCL-b-PEG: Synthesis, Characterization, and Potential as Efficient Nonviral Gene Delivery Vectors. *Macromolecules* 36, 5751-5759 (2003).

Sun L, et al., Human beta-defensins suppress human immunodeficiency virus infection: potential role in mucosal protection. J Virol, 2005. 79(22):14318-29.

Klotman Me and Chang TL. Defensins in innate antiviral immunity. Nat Rev Immunol, 2006. 6(6):447-56.

Biragyn A, et al. Toll-like receptor 4-dependent activation of dendritic cells by beta-defensin 2. Science, 2002. 298(5595):1025-9.

Becker MN, et al. CD14-dependent lipopolysaccharide-induced beta-defensin-2 expression in human tracheobronchial epithelium. J Biol Chem, 2000. 275(38):29731-6.

Rivas-Santiago B, et al. beta-Defensin gene expression during the course of experimental tuberculosis infection. J Infect Dis, 2006. 194(5):697-701.

Chong KT, Thangavel RR, Tang X. Enhanced expression of murine beta-defensins (MBD-1, -2,- 3, and -4) in upper and lower airway mucosa of influenza virus infected mice. Virology, 2008. 380(1):136-43.

\* cited by examiner

FIG. 3A

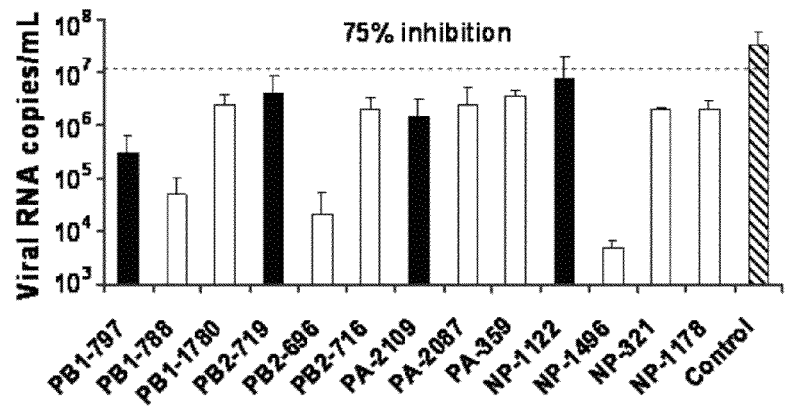

FIG. 3B

| Names | Targets | Sequences 5' – 3' |
| --- | --- | --- |
| PB1-797 | PB1 | F: UUGAGCAAUCUGGACUCCdTdT<br>R: GGGAGUCCAGAUUGCUCAAdTdT |
| PB1-788 | PB1 | F: GUGAGAAACUUGAGCAAUCdTdT<br>R: GAUUGCUCAAGUUUCUCACdTdT |
| PB2-719 | PB2 | F: GGGAACAGAUGUACACUCCdTdT<br>R: GGAGUGUACAUCUGUUCCCdTdT |
| PB2-696 | PB2 | F: GCAUUUGACUCAAGGGACCdTdT<br>R: GGUCCCUUGAGUCAAAUGCdTdT |
| PA-2109 | PA | F: GGUUCAACUCCUUCCUCGCdTdT<br>R: GCGAGGAAGGAGUUGAACCdTdT |
| PA-2087* | PA | F: GCAAUUGAGGAGUGCCUGAdTdT<br>R: UCAGGCACUCCUCAAUUGCdTdT |
| NP-1122 | NP | F: GGACUCCAACACUCUUGAAdTdT<br>R: UUCAAGAGUGUUGGAGUCCdTdT |
| NP-1496* | NP | F: GGAUCUUAUUUCUUCGGAGdTdT<br>R: CUCCGAAGAAAUAAGAUCCdTdT |
| PB2-1291 | PB2 | F: AUGCAUCAACUCCUGAGACdTdT<br>R: GUCUCAGGAGUUGAUGCAUdTdT |

```
                          5'                          3'
A/Hong Kong/156/97:  GGUUCAACUCCUUCCUCAC.

A/Shen Zhen/406H:    GGUUCAACUCCUUCCUCAC..

siRNA PA-2109        GGUUCAACUCCUUCCUCGC
```

SIRNA COMPOSITIONS AND METHODS FOR POTENTLY INHIBITING VIRAL INFECTION

CROSS-REFERENCE TO RELATED APPLICATIONS

This application is a divisional of U.S. application Ser. No. 12/636,234, filed Dec. 11, 2009, now U.S. Pat. No. 8,664,188 which claims priority to U.S. Provisional Application No. 61/121,614, filed Dec. 11, 2008, the disclosures of which are hereby incorporated by reference in their entirety.

BACKGROUND OF THE INVENTION

Recent outbreaks of highly pathogenic H5N1 avian flu virus infection in poultry and humans have raised concerns that a new influenza pandemic may occur in the near future[1]. Considering the high mortality associated with H5N1 avian flu, which has ranged from 45% to 81%[2,3], and the limited efficacy of current vaccines and drugs[4,5], development of novel strategies for prevention and treatment of avian flu H5N1 viral infection is urgently needed.

H5N1 avian flu virus belongs to influenza A virus, which is an enveloped, negative-stranded RNA virus. The unique property of being a single-stranded RNA virus makes it attractive to use small interfering RNAs (siRNAs) as anti-avian flu prophylactics and therapeutics. siRNAs are double stranded RNA duplexes that mediate sequence-specific degradation of mRNA when bound with the RNA-induced silencing complex (RISC) through antisense strand[6,7]. It has been reported that siRNAs targeting PA and NP genes of H5N1 virus can effectively inhibit viral replication in cultured cells and provide a prophylactic effect in a mouse model, but cannot offer any significant therapeutic effect[8,9]. Therefore, design and identification of more effective siRNAs are urgently needed for the development of RNA interference-based anti-H5N1 agents.

BRIEF SUMMARY OF THE INVENTION

We designed and characterized 25 candidate siRNAs targeting relatively conserved region of H5N1 viral genes PB1, PB2, PA, NP, M, NS and HA. Interestingly, several effective siRNAs, which are distinct from any other reported siRNAs[8-13], contain a novel motif (these are designated "siRNA-m"). Compared to siRNAs that do not contain this motif (designated "siRNA-n"), including two siRNAs that have been reported to be most effective both in cultured cells and in vivo[8,9], these siRNAs showed less antiviral effects in cell culture assays but surprisingly provided much higher protection against lethal challenge of highly pathogenic influenza virus isolates in a mouse model. Furthermore, the strong in vivo protection can be associated with early productions of β-defensin and IL-6 induced by the motif. Novel viral inhibitors are thus provided. New methods of screening for potential anti-viral agents are provided. Also provided are methods of making potent viral inhibitors, as well as methods of prevention, inhibition, and treatment of viral infection and proliferation.

BRIEF DESCRIPTION OF THE DRAWINGS

FIG. 3 represents screening for effective siRNAs that inhibit H5N1 influenza A virus infection in cell cultures. (a) Antiviral effects of 25 siRNAs in cell culture. MDCK cells were transfected with chemically synthesized siRNAs for 12 h, and then infected with 100 $TCID_{50}$ of H5N1 A/Vietnam/1194/04 strain for 48 h. Cell supernatants were collected for real time RT-PCR to detect the viral RNA copies. Twelve siRNAs, including 4 siRNAs-m (black) and 6 siRNAs-n (white) that were newly designed, as well as 2 positive control siRNAs that were reported previously to be effective[8,9], showed more than 75% inhibition which is indicated with a dashed line. (b) Sequences of selected siRNAs-m and siRNAs-n and identification of a unique motif. The sequence motif identified in siRNAs-m is underlined in forward strand (F) and boxed in reverse strand (R). The motif in a small RNA PB2-1291 is also highlighted.

BRIEF DESCRIPTION OF THE SEQUENCES

SEQ ID NO: 1 is the forward sequence of siRNA-n "PB 1-666"

SEQ ID NO: 2 is the forward sequence of siRNA-n "PB1-788"

SEQ ID NO: 3 is the forward sequence of siRNA-m "PB 1-797"

SEQ ID NO: 4 is the forward sequence of siRNA-n "PB1-1688"

SEQ ID NO: 5 is the forward sequence of siRNA-n "PB1-1780"

SEQ ID NO: 6 is the forward sequence of siRNA-n "PB2-696"

SEQ ID NO: 7 is the forward sequence of siRNA-m "PB2-719"

SEQ ID NO: 8 is the forward sequence of siRNA-n "PB2-1558"

SEQ ID NO: 9 is the forward sequence of siRNA-n "PB2-18318"

SEQ ID NO: 10 is the forward sequence of siRNA-n "PA-209"

SEQ ID NO: 11 is the forward sequence of siRNA-n "PA-359"

SEQ ID NO: 12 is the forward sequence of siRNA-n "PA-2036"

SEQ ID NO: 13 is the forward sequence of siRNA-reported "PA-2087"

SEQ ID NO: 14 is the forward sequence of siRNA-m "PA-2109"

SEQ ID NO: 15 is the forward sequence of siRNA-n "NP-321"

SEQ ID NO: 16 is the forward sequence of siRNA-m "NP-1122"

SEQ ID NO: 17 is the forward sequence of siRNA-n "NP-1178"

SEQ ID NO: 18 is the forward sequence of siRNA-reported "NP-1496"

SEQ ID NO: 19 is the forward sequence of siRNA-n "HA-869"

SEQ ID NO: 20 is the forward sequence of siRNA-n "HA-855"

SEQ ID NO: 21 is the forward sequence of siRNA-n "M-97"

SEQ ID NO: 22 is the forward sequence of siRNA-n "M-101"

SEQ ID NO: 23 is the forward sequence of siRNA-n "M-925"

SEQ ID NO: 24 is the forward sequence of siRNA-n "NS-338"

SEQ ID NO: 25 is the forward sequence of siRNA-n "NS-604"

SEQ ID NO: 26 is the forward sequence of siRNA-n "NS-677"

SEQ ID NO: 27 is the forward sequence of siRNA-n "NS-782"

SEQ ID NO: 28 is the reverse sequence of siRNA-m "PB 1-797"

SEQ ID NO: 29 is the reverse sequence of siRNA-n "PB1-788"

SEQ ID NO: 30 is the reverse sequence of siRNA-m "PB2-719"

SEQ ID NO: 31 is the reverse sequence of siRNA-n "PB2-696"

SEQ ID NO: 32 is the reverse sequence of siRNA-m "PA-2109"

SEQ ID NO: 33 is the reverse sequence of siRNA-reported "PA-2087"

SEQ ID NO: 34 is the reverse sequence of siRNA-m "NP-1122"

SEQ ID NO: 35 is the reverse sequence of siRNA-reported "NP-1496"

SEQ ID NO: 36 is the forward sequence in a small RNA "PB2-1291"

SEQ ID NO: 37 is the reverse sequence in a small RNA "PB2-1291"

DETAILED DISCLOSURE OF THE INVENTION

Figure 4A:
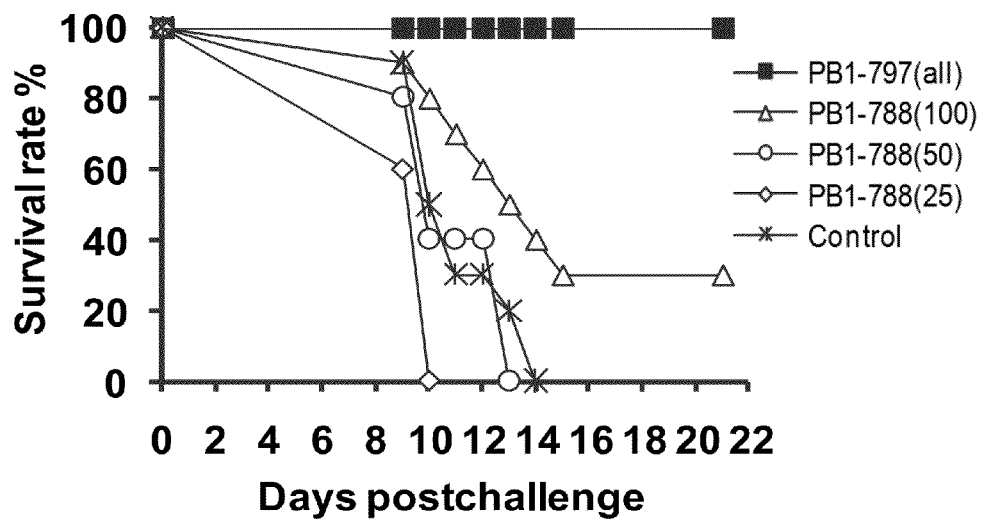
FIG. 4 graphically depicts evaluation of in vivo antiviral effects of siRNAs-m and siRNAs-n. (a), (b), (c) and (d) Evaluation of prophylactic effect of 4 paired siRNAs-m and siRNAs-n respectively targeting viral PB1, PB2, PA and NP genes. Mice were i.t. administered one dose of 100, 50 or 25 µg (indicated in brackets) siRNAs-m or siRNAs-n 16-18 h before viral challenge. Control mice (control) were given PBS and/or PEGS-PEI1.8. Survival, body weight and general conditions were monitored for 21 days or until death. (e), (f), (g) (h) and (j) Monitoring of body weight in mice treated with siRNAs-m and siRNAs-n. Body weights of these mice were monitored for 21 days or until death. (i) Evaluation of therapeutic effect of siRNA-m and siRNA-n. Mice were i.n. given 4 doses of NP-1122 (siRNA-m) or NP-1496 (siRNA-n) 24 hrs post-challenge. Control mice (control) were given PEGS-PEI1.8. Survival, body weight and general conditions were monitored for 21 days or unstill death.
Figure 4B:
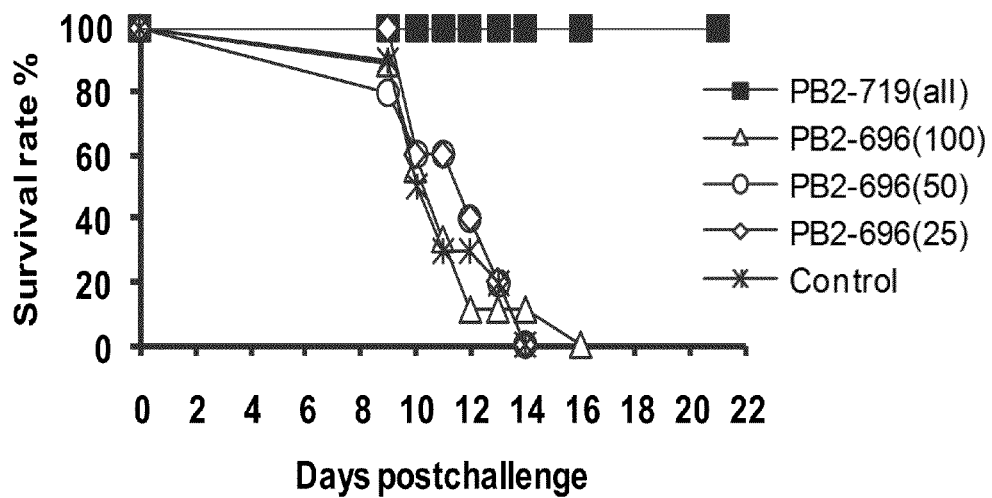
Figure 4C:
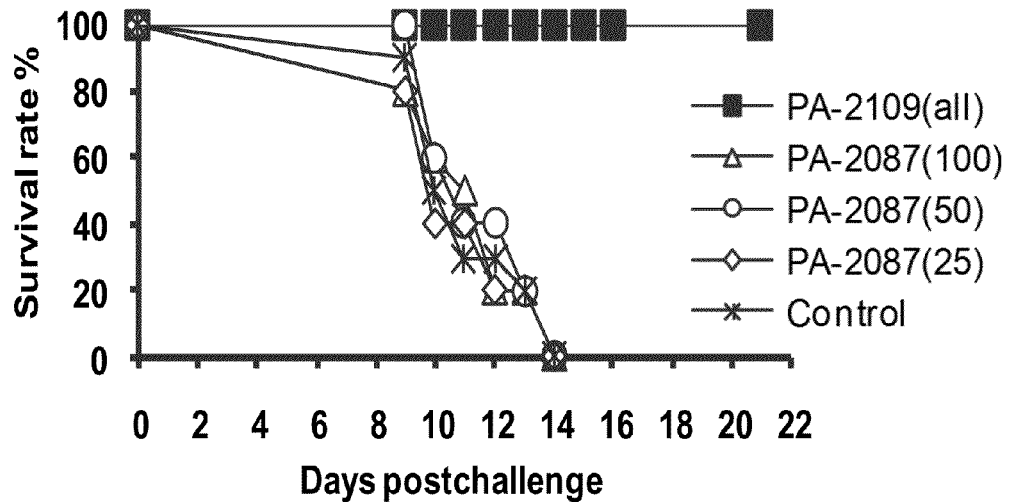
Figure 4D:
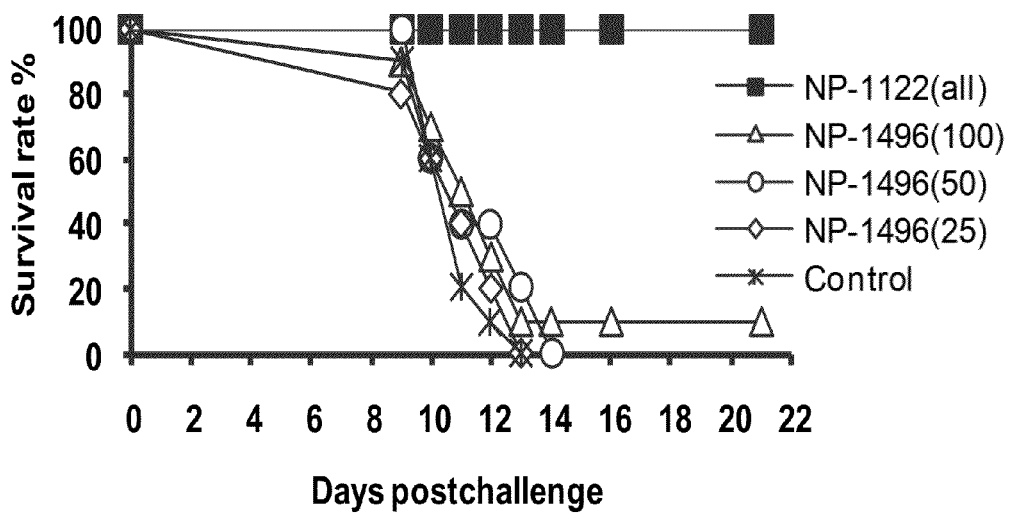
Figure 4E:
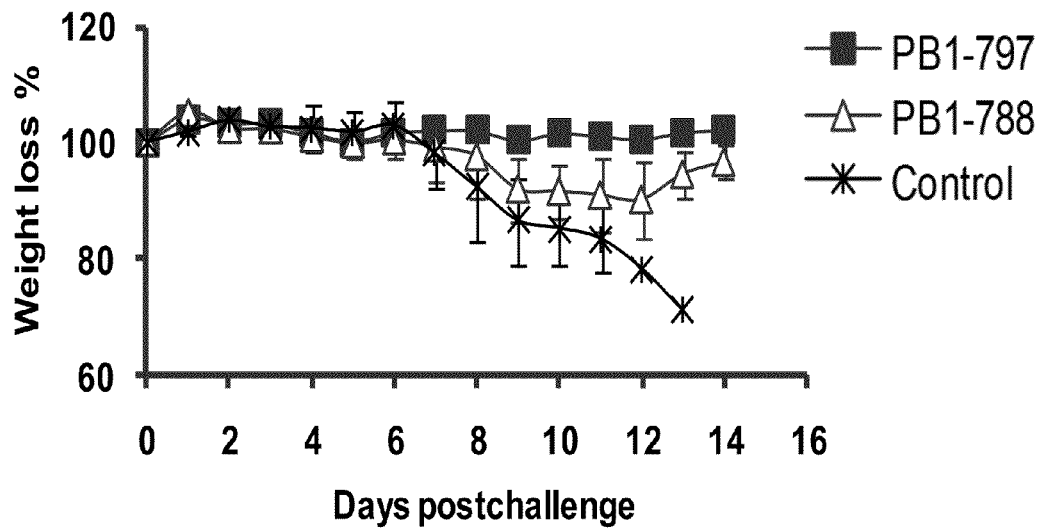
Figure 4F:
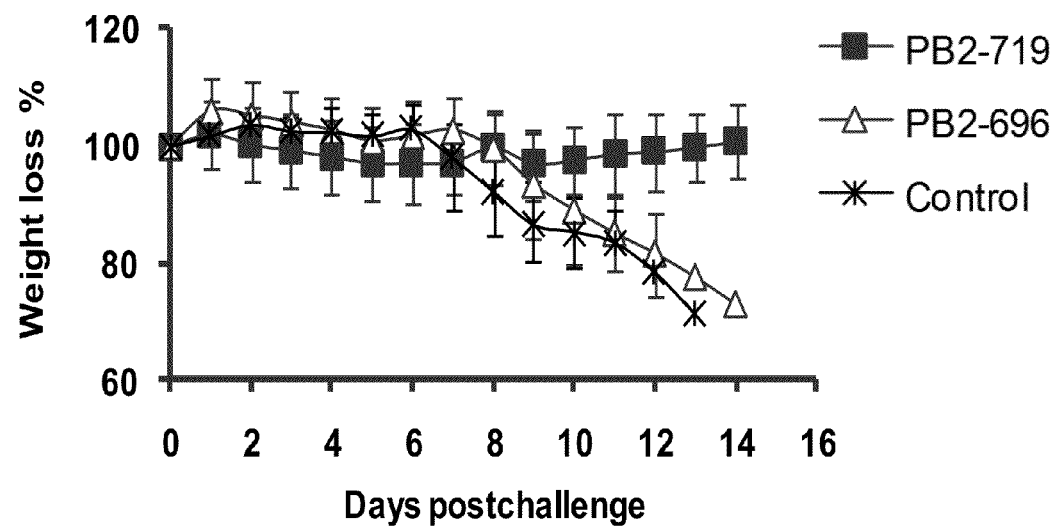
Figure 4G:
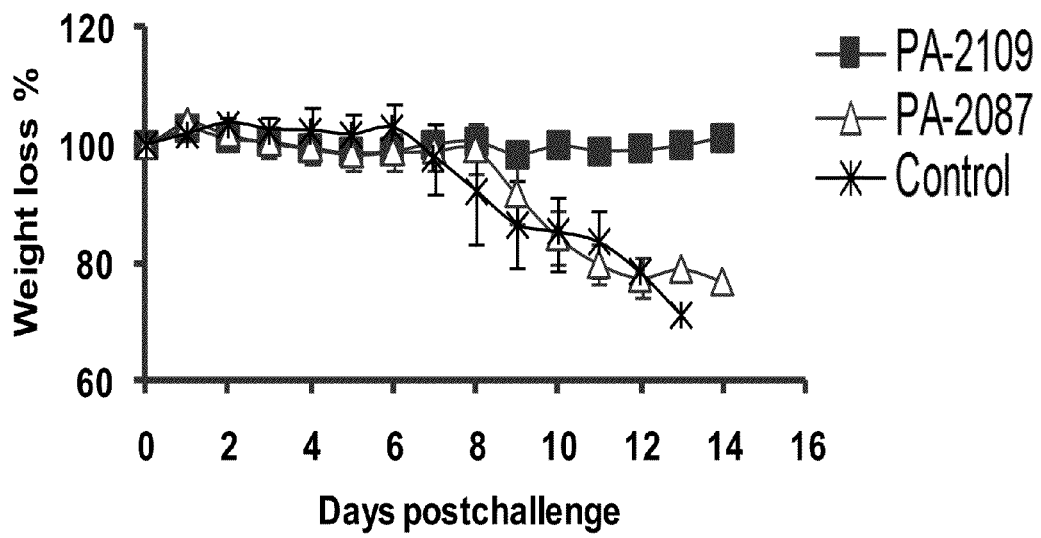
Figure 4H:
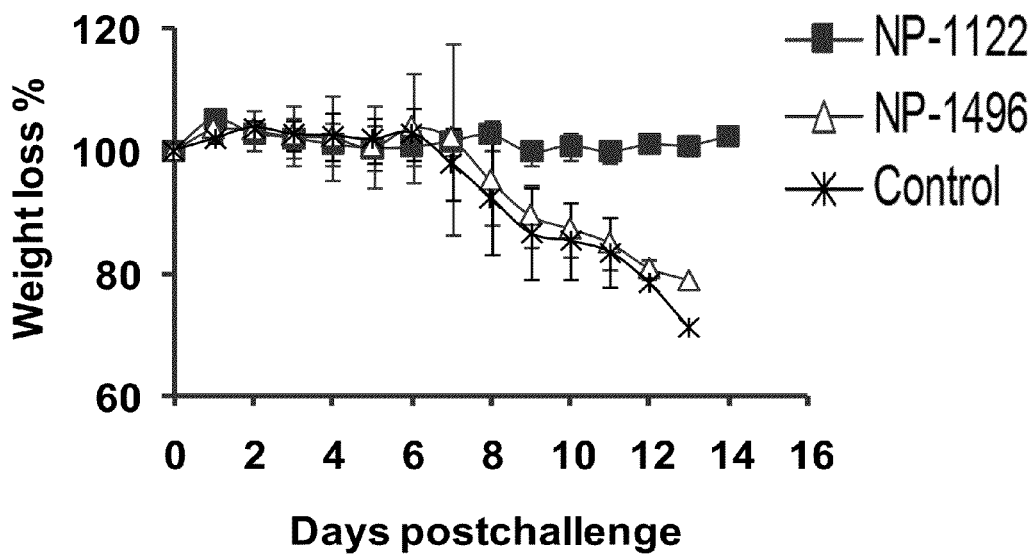
Figure 4I:
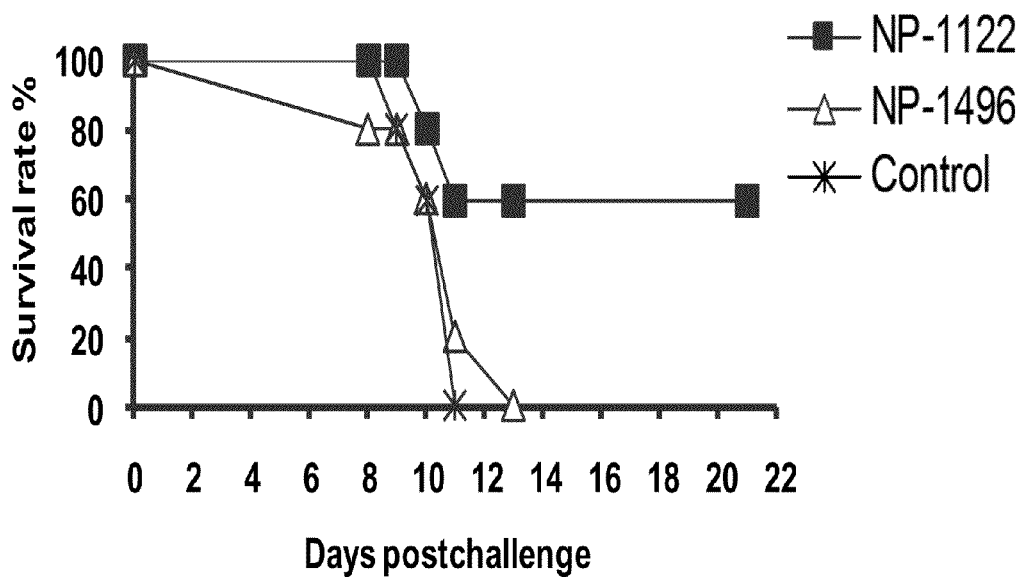
Figures 6A, 6B:
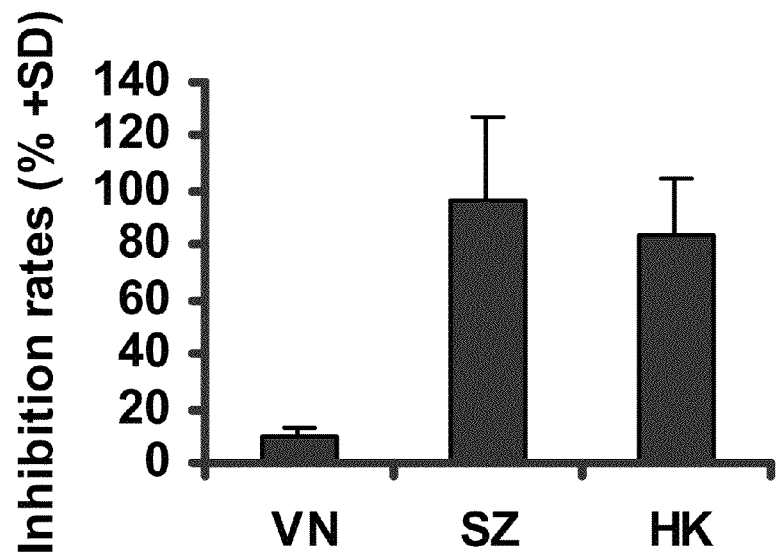
FIG. 6 explores roles of the unique motif in determining the potency of in vivo antiviral effects. (a) Sequences of a selected siRNA-m (PA-2109) and the corresponding region in different H5N1 virus strains. One mismatched nt was found (bold) by sequence comparison. (b) Cross-strain antiviral effects of the siRNA-m in cell culture. Antiviral effects of PA-2109 against perfectly matched virus strain A/Vietnam/1194/2004 (VN) as well as imperfectly matched virus strains A/Shenzhen/406H (SZ) and A/Hong Kong/156/97 (HK) were detected by measuring viral RNA copies in culture supernatants collected 48 h post-infection using real-time RT-PCR. The results are presented as inhibition rates of the siRNA-m against different virus strains as compared to their untreated controls. (c) and (d) Cross-protection of the siRNA-m was evaluated in animals respectively challenged with imperfectly matched virus strains. Mice were given one dose of 25 µg PA-2109 and respectively challenged with 10 $LD_{50}$ of A/Shenzhen/406H and A/Hong Kong/156/97 16-18 h post-treatment. (e) In vivo antiviral effect of a small RNA containing the motif. Mice were administered with one dose of PB2-1291, which is not an optimal siRNA according to generally accepted criteria but contains the motif, and then infected with H5N1 virus strain A/Vietnam/1194/2004 after 16-18 h. Control mice (control) for these experiments (c, d and e) were given PEG8-PEI1.8. Survival, body weight and general conditions were monitored for 21 days or until death and (f) Weight loss of the mice in the experiment described above in (c) and (d). (g) In vivo antiviral effect of a small RNA containing the motif. Mice were administered with one dose of PB2-1291, which is not an optimal siRNA according to generally accepted criteria but contains the motif, and then infected with H5N1 virus strain A/Vietnam/1194/2004 after 16-18 h. (h) Weight loss of the mice described in (g). Control mice (control) for these experiments (c, d, e, f. g and h) were given PEG8-PEI1.8. Survival weight and general conditions were monitored for 21 days or until death.

We have discovered a unique motif shared by siRNAs that potently inhibit H5N1 influenza A virus infection in vivo. Using an accepted mouse model of infection with highly virulent human H5N1 virus strain A/Vietnam/1194/04$_{(17)}$, we demonstrated that the siRNAs-m have a potent in vivo protective effect. For prophylaxis, even when the animals were given as low as 25 µg of siRNAs-m, they could still fully protect (100% survival) the experimental animals from lethal challenge of H5N1 virus, whereas siRNAs-n, including the two siRNAs that have been reported to be able to fully protect the mice from the lethal challenge of several other influenza virus strains$_{(9)}$, provided little or no protection for the animals even though they were given 100 µg of the siRNAs-n (FIG. 4a, b, c & d). For therapy, our study indicated that 60% animals receiving siRNA-m at 24 hours after the viral challenge survived, but all mice given siRNA-n died (FIG. 4i). This is the best therapeutic effect mediated by siRNAs as reported so far$_{(8,18,19)}$, and it is likely that even better effects can be achieved by routine optimization of the delivery system, administration route, and dosage of the siRNAs-m. Furthermore, the siRNAs-m may provide full cross-protection against the lethal challenge of two imperfectly matched H5N1 virus strains (FIGS. 6c & 6d), indicating that the siRNAs-m can even be capable of targeting mutated viruses. Considering the rapid mutations of influenza A virus, these siRNAs-m can be highly effective prophylactic and therapeutic agents.

As used herein, the term "isolated" molecule (e.g., isolated nucleic acid molecule) refers to molecules which are substantially free of other cellular material, or culture medium when produced by recombinant techniques, or substantially free of chemical precursors or other chemicals when chemically synthesized. In addition, an isolated molecule such as a nucleic acid molecule is considered "isolated" if by virtue of the activity of a human it is in a condition, context, or composition that is different from how it is found in nature.

As used herein, an "effective amount" of siRNA is that amount effective to bring about the physiological changes desired in the cells to which the siRNA is administered in vitro (e.g., ex vivo) or in vivo. The term "therapeutically effective amount" as used herein means that amount of an siRNA alone or in combination with another agent according to the particular aspect of the invention, that elicits the biological or medicinal response in cells (e.g., tissue(s)) that is being sought by a researcher, veterinarian, medical doctor or other clinician, which includes alleviation and/or prevention and/or inhibition of the symptoms of the disease or disorder being treated.

Various methods of the present invention can include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing a siRNA of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Reduction (suppression) of virus results in a decrease (or prevention) of viral load. For example, in a cell culture, the suppression of virus by administration of siRNA results in a decrease in the quantity of virus relative to an untreated cell culture. Suppression may be partial. Preferred degrees of suppression are at least 50%, more preferably one of at least 60%, 70%, 80%, 85%, or 90%, and most preferably between 90% and 100%.

The terms "treatment" and "therapy" are used interchangeably herein, and as used herein include both prophylactic and responsive treatment, can be either acute short-term or chronic long-term, and denote the inhibition or amelioration of viral infection in a patient. "Patient" includes animals, including humans. The term "therapeutically effective" means that the amount of therapeutic agent (siRNA) used is of sufficient quantity to inhibit or ameliorate the symptoms of viral infection.

RNA Interference

RNAi is an efficient process whereby double-stranded RNA (dsRNA, also referred to herein as siRNAs or ds siRNAs, for double-stranded small interfering RNAs) induces the sequence-specific degradation of targeted single-stranded RNA in animal and plant cells (Hutvagner and Zamore, *Curr. Opin. Genet. Dev.*: 12, 225-232 (2002); Sharp, *Genes Dev.*, 15:485-490 (2001)). In mammalian cells, RNAi can be triggered by 21-nucleotide (nt) duplexes of small interfering RNA (siRNA) (Chiu et al., *Mol. Cell.* 10:549-561 (2002); Elbashir et al., *Nature* 411:494-498 (2001)), or by microRNAs (miRNA), functional small-hairpin RNA (shRNA), or other dsRNAs which can be expressed in vivo using DNA templates with RNA polymerase III promoters (Zeng et al., *Mol. Cell.* 9:1327-1333 (2002); Paddison et al., *Genes Dev.* 16:948-958 (2002); Lee et al., *Nature Biotechnol.* 20:500-505 (2002); Paul et al., *Nature Biotechnol.* 20:505-508 (2002); Tuschl, T., *Nature Biotechnol.* 20:440-448 (2002); Yu et al., *Proc. Natl. Acad. Sci. USA* 99(9):6047-6052 (2002); McManus et al., *RNA* 8:842-850 (2002); Sui et al., *Proc. Natl. Acad. Sci. USA* 99(6):5515-5520 (2002)), each of which are incorporated herein by reference in their entirety.

The scientific literature contains many reports of endogenous and exogenous gene expression silencing using siRNA, highlighting their therapeutic potential (Gupta, S. et al. PNAS, 2004, 101:1927-1932; Takaku, H. *Antivir Chem. Chemother*, 2004, 15:57-65; Pardridge, W. M. *Expert Opin.*

*Biol. Ther.*, 2004, 4:1103-1113; Zheng, B. J. *Antivir. Ther.*, 2004, 9:365-374; Shen, W. G. *Chin. Med. J. (Engl)*, 2004, 117:1084-1091; Fuchs, U. et al. *Curr. Mol. Med.*, 2004, 4:507-517; Wadhwa, R. et al. *Mutat. Res.*, 2004, 567:71-84; Ichim, T. E. et al. *Am. J. Transplant*, 2004, 4:1227-1236; Jana, S. et al. *Appl. Microbiol. Biotechnol.*, 2004, 65:649-657; Ryther, R. C. et al. *Gene Ther.*, 2005, 12:5-11; Chae, S-S. et al., *J. Clin. Invest.*, 2004, 114:1082-1089; Fougerolles, A. et al., *Methods Enzymol.*, 2005, 392:278-296), each of which is incorporated herein by reference in its entirety. Therapeutic silencing of endogenous genes by systemic administration of siRNAs has been described in the literature (Kim B. et al., *American Journal of Pathology*, 2004, 165:2177-2185; Soutschek J. et al., *Nature*, 2004, 432:173-178; Pardridge W. M., *Expert Opin. Biol. Ther.*, 2004, July, 4(7):1103-1113), each of which is incorporated herein by reference in its entirety.

Accordingly, the invention includes such interfering RNA molecules that are targeted to viruses, influenza A viruses, and especially H5N1 viruses. The interfering RNA may be a double-stranded siRNA. As the skilled person will appreciate, and as explained further herein, an siRNA molecule may include a short 3' DNA sequence also. Alternatively, the nucleic acid may be a DNA (usually double-stranded DNA) which, when transcribed in a cell, yields an RNA having two complementary portions joined via a spacer, such that the RNA takes the form of a hairpin when the complementary portions hybridize with each other. In a mammalian cell, the hairpin structure may be cleaved from the molecule by the enzyme Dicer, to yield two distinct, but hybridized, RNA molecules.

In one embodiment, the invention provides an interfering RNA that is capable, when suitably introduced to or expressed within cells that may be subject to viral challenge, suppresses viral load expression by RNAi, wherein the interfering RNA is generally targeted to the virus. Preferably, the interfering RNA sequence is within the range of about 19 to 23 nucleotides. For example, in those embodiments in which an shRNA is utilized, that portion of the shRNA targeting the virus is preferably within the range of about 19 to 23 nucleotides.

As explained herein, perfect identity/complementarity between the interfering RNA used in the method of the invention and the target viral sequence, although sometimes preferred, is not essential. Accordingly, the interfering RNA may include some mismatches as compared to the target viral sequence.

siRNA Molecules

Short interfering RNAs (siRNAs) induce the sequence-specific suppression or silencing (i.e., reducing expression which may be to the extent of partial or complete inhibition) genes by the process of RNAi. Thus, siRNA acts as an effector molecule of the RNAi process. The siRNA molecules that function as viral inhibitors can be chemically synthesized, or can be transcribed in vitro from a DNA template, or in vivo from, e.g., shRNA. The dsRNA molecules can be designed using any method known in the art, for instance, by using the following protocol:

1. Using any method known in the art, compare the potential targets to the appropriate genome database (human, mouse, rat, etc.) and eliminate from consideration any target sequences with significant homology to other coding sequences. One such method for sequence homology searches is known as BLAST, which is available at the National Center for Biotechnology Information (NCBI) web site of the National Institutes of Health. Also available on the NCBI webs site is the HomoloGene database, which is a publicly available system for automated detection of homologs among the annotated genes of several completely sequenced eukaryotic genomes and is readily utilized by those of ordinary skill in the art.

2. Select one or more sequences that meet your criteria for evaluation. Further general information regarding the design and use of siRNA can be found in "The siRNA User Guide," available at the web site of the laboratory of Dr. Thomas Tuschl at Rockefeller University (Elbashir et al., *EMBO J.,* 2001, 20:6877-6888).

3. Negative control siRNAs preferably have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can sometimes be designed by introducing one or more base mismatches into the sequence.

Initially, basic criteria were defined for identification of efficient siRNA, such as GC content and position of the targeted sequence in the context of the mRNA (Elbashir S M. et al., *Methods,* 2002, 26:199-213). Further progress was achieved more recently, when the assembly of the RNAi enzyme complex was described as being dependent on thermodynamic characteristics of the siRNA (Khrvorova A. et al., *Cell,* 2003, 115:209-216; Schwarz D. S. et al., *Cell,* 2003, 115:199-208). The relative stability of both ends of the duplex was determined to have effects on the extent to which the individual strands enter the RNAi pathway. In addition, certain sequence motifs at defined positions of the siRNA were reported to influence its potency (Amarzguioui M. and H. Prydz, *Biochem. Biophys. Res. Commun.,* 2004, 316:1050-1058; Reynolds A. et al., *Nature Biotechnol.,* 2004, 22:326-330). On this basis, sophisticated algorithms have been developed to increase the success rate of siRNA design and are available to those skilled in the art (Amarzguioui M. and H. Prydz, 2004; Reynolds A. et al., 2004; and Ui-Tei K. et al., *Nucl. Acids Res.,* 2004, 32:936-948, each of which is incorporated herein in its entirety).

Other computational tools that may be used to select siRNAs of the present invention include the Whitehead siRNA selection Web Server from the bioinformatics group at the Whitehead Institute for Biomedical Research in Cambridge, Mass., and other disclosed in Yuan, B. et al. ("siRNA Selection Server: an automated siRNA oligonucleotide prediction server", *Nucleic Acids Research,* 2004, Vol. 32, W130-W134, Web Server issue) and Bonetta L. ("RNAi: Silencing never sounded better", *Nature Methods*, October, 2004, 1(1):79-86), each of which are incorporated by reference herein in their entirety.

As shown herein, the efficiencies of different siRNAs may differ significantly. However, strategies for rational design of effective interfering RNA exist (Gong D. and J. E. Ferrell Jr., TRENDS in Biotechnology, 2004, 22(9):451; Schubert S. et al., J. Mol. Biol., 2005, 348:883-893; Pancoska P. et al., Nucleic Acids Research, 2004, 32(4):1469-1479; Mittal V., *Nat. Rev. Genet.,* 2004, 5(5):355-365, each of which is incorporated herein by reference in its entirety).

Screening for the most efficient siRNAs using cell cultures may be carried out. Several in vitro screening methods based on the use of siRNA mixtures, which may contain a particular efficient siRNA (or several), have been developed. These include the preparation of siRNA mixtures using RNase III or Dicer enzymes to digest longer double-stranded RNAs, such as BLOCK-IT products (INVITROGEN, Carlsbad Calif.) (Yang D. et al., *Proc. Natl. Acad. Sci. USA,* 2002, 99:9942-

9947; Myers J. W. et al., *Nat. Biotechnol.,* 2003, 21:324-328). The short RNAs produced as a result of these digestions have been found to be efficient in RNAi. Oligonucleotide arrays can also be used for the efficient preparation of defined mixtures of siRNAs for reducing the expression of exogenous and endogenous genes such as PKC-ι (Oleinikov A. V. et al., *Nucleic Acids Research,* 2005, 33(10):e92).

The viral inhibitors of the invention can include both unmodified siRNAs and modified siRNAs as known in the art. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The viral inhibitors of the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., *Drug Deliv. Rev.* 47(1): 99-112 (2001) (describes nucleic acids loaded to polyalkylcyanoacrylate (PACA) nanop articles); Fattal et al., *J. Control Release* 53(1-3): 137-43 (1998) (describes nucleic acids bound to nanoparticles); Schwab et al., *Ann. Oncol.* 5 Suppl. 4:55-8 (1994) (describes nucleic acids linked to intercalating agents, hydrophobic groups, polycations or PACA nanoparticles); and Godard et al., *Eur. J. Biochem.* 232(2):404-10 (1995) (describes nucleic acids linked to nanoparticles).

The viral inhibitors of the present invention can also be labeled using any method known in the art; for instance, nucleic acids can be labeled with a fluorophore, e.g., Cy3, fluorescein, or rhodamine. The labeling can be carried out using a kit, e.g., the SILENCER siRNA labeling kit (AMBION). Additionally, the siRNA can be radiolabeled, e.g., using $^3$H, $^{32}$P, or other appropriate isotope.

Because RNAi is believed to progress via at least one single stranded RNA intermediate, the skilled artisan will appreciate that ss-siRNAs (e.g., the antisense strand of a ds-siRNA) can also be designed as described herein and utilized according to the claimed methodologies.

There are a number of companies that will generate interfering RNAs for a specific gene. Thermo Electron Corporation (Waltham, Mass.) has launched a custom synthesis service for synthetic short interfering RNA (siRNA). Each strand is composed of 18-20 RNA bases and two DNA bases overhang on the 3' terminus. Dharmacon, Inc. (Lafayette, Colo.) provides siRNA duplexes using the 2'-ACE RNA synthesis technology. Qiagen (Valencia, Calif.) uses TOM-chemistry to offer siRNA with high individual coupling yields (Li, B. et al., *Nat. Med.,* 2005, 11(9), 944-951).

siRNA Delivery for Longer-Term Expression

Synthetic siRNAs can be delivered into cells by methods known in the art, including cationic liposome transfection (LIPOFECTAMINE 2000 reagent, for example) and electroporation, for example. However, these exogenous siRNA generally show short term persistence of the silencing effect (4 to 5 days in cultured cells), which may be beneficial in certain embodiments. To obtain longer suppression of viral expression and to facilitate delivery under certain circumstances, one or more siRNA duplexes, e.g., H5N1 ds siRNA-m, can be expressed within cells from recombinant DNA constructs (McIntyre G. J. and G. C. Fanning, *BMC Biotechnology,* 2006, 6:1-8). Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl (2002), supra) capable of expressing functional double-stranded siRNAs; (Bagella et al., *J. Cell. Physiol.* 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by an H1 or U6 snRNA promoter can be expressed in cells, and can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence(s) under the control of a T7 promoter also make functional siRNAs when co-transfected into the cells with a vector expressing T7 RNA polymerase (Jacque (2002), supra). A single construct may contain multiple sequences coding for siRNAs, such as multiple regions of viral RNA, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng (2002), supra). When expressed by DNA vectors containing polymerase III promoters, micro-RNA designed hairpins can silence gene expression (McManus (2002), supra). Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari et al., *Proc. Natl. Acad. Sci. USA* 99(22):14236-40 (2002)). In adult mice, efficient delivery of siRNA can be accomplished by the "high-pressure" delivery technique, a rapid injection (within 5 seconds) of a large volume of siRNA containing solution into animal via the tail vein (Liu (1999), supra; McCaffrey (2002), supra; Lewis, *Nature Genetics* 32:107-108 (2002)). Nanoparticles, liposomes and other cationic lipid molecules can also be used to deliver siRNA into animals. It has been shown that siRNAs delivered systemically in a liposomal formulation can silence the disease target apolipoprotein B (ApoB) in non-human primates (Zimmermann T. S. et al., *Nature*, 2006, 441:111-114). A gel-based agarose/liposome/siRNA formulation is also available (Jiamg M. et al., *Oligonucleotides*, 2004, Winter, 14(4):239-48).

Uses of Engineered RNA Precursors to Induce RNAi

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the virus to be targeted by the siRNA generated from the engineered RNA precursor will be depleted from the cell or organism, leading to a decrease in the concentration of any translational product encoded by that mRNA in the cell or organism. The RNA precursors are typically nucleic acid molecules that individually encode either one strand of a dsRNA or encode the entire nucleotide sequence of an RNA hairpin loop structure.

Pharmaceutical Compositions and Methods of Administration

The viral inhibitors of the subject invention can be incorporated into pharmaceutical compositions. Such compositions typically include the viral inhibitor and a pharmaceutically acceptable carrier. As used herein, the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions. Formulations (compositions) are described in a number of sources that are well known and readily available to those skilled in the art. For example, *Remington's Pharmaceutical Sciences* (Martin E. W., Easton Pa., Mack Publishing Company, 19$^{th}$ ed., 1995) describes formulations which can be used in connection with the subject invention.

A pharmaceutical composition is formulated to be compatible with its intended route of administration. Examples of routes of administration include parenteral, e.g., intravenous, intradermal, subcutaneous, oral (e.g., inhalation), topical, transdermal, transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL (BASF, Parsippany, N.J.) or phosphate buffered saline (PBS). In all cases, the composition must be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as manitol, sorbitol, sodium chloride can also be included in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polynucleotide of the invention) in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, suitable methods of preparation include vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the subject viral inhibitors can be delivered in the form of an aerosol spray from a pressurized container or dispenser which contains a suitable propellant, e.g., a gas such as carbon dioxide, or a nebulizer. Such inhalation methods and inhalant formulations include those described in U.S. Pat. No. 6,468,798.

Systemic administration of viral inhibitors can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compound (e.g., polynucleotides of the invention) are formulated into ointments, salves, gels, or creams, as generally known in the art.

The pharmaceutical compositions can also be prepared in the form of suppositories (e.g., with conventional suppository bases such as cocoa butter and other glycerides) or retention enemas for rectal delivery.

The viral inhibitors can also be administered by transfection or infection using methods known in the art, including but not limited to the methods described in McCaffrey et al., *Nature* 418(6893):38-39 (2002) (hydrodynamic transfection); Xia et al., *Nature Biotechnol.* 20(10):1006-10 (2002) (viral-mediated delivery); or Putnam, *Am. J. Health Syst. Pharm.* 53(2):151-160 (1996), erratum at *Am. J. Health Syst. Pharm.* 53(3):325 (1996).

Viral inhibitors that are polynucleotides can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in Hamajima et al., *Clin. Immunol. Immunopathol.* 88(2):205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the polynucleotide viral inhibitors are prepared with carriers that will protect the polynucleotide against rapid elimination from, or degradation in, the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions (including liposomes targeted to antigen-presenting cells with monoclonal antibodies) can also be used as pharmaceutically acceptable carriers. These can be prepared according to methods known to those skilled in the art, for example, as described in U.S. Pat. No. 4,522,811. Strategies that inhibit members of the RNAse A family of enzymes or can otherwise protect the subject polynucleotide viral inhibitors from these enzymes may be utilized. For example, U.S. Pat. No. 6,096,720 (Love et al.) describes oligonucleotides targeted to human raf mRNA, which are entrapped in sterically stabilized liposomes. In one embodiment, the oligonucleotide in Love et al. is a chimeric oligonucleotide containing a first region to enhance target affinity and a second region that is a substrate for RNase. siSHIELD RNAse inhibitor is designed to prevent degradation of siRNA by RNase (MP BIOMEDICALS, Irvine, Calif.). A strategy for the compaction of short oligonucleotides into well-defined condensates may also be used to deliver the polynucleotides of the subject invention (Sarkar T. et al., *Nucleic Acids Research*, 2005, 33(1):143-151), which is incorporated herein by reference in its entirety.

In particular, suitable techniques for cellular administration of the polynucleotide viral inhibitors, such as interfering RNA, in vitro or in vivo are disclosed in the following articles:
General Reviews:
 Borkhardt, A. *Cancer Cell*, 2002, 2:167-8; Hannon, G. J. *Nature*, 2002, 418:244-51; McManus, M. T. and Sharp, P. A. *Nat Rev Genet.*, 2002, 3:737-47; Scherr, M. et al. *Curr Med. Chem.*, 2003, 10:245-56; Shuey, D. J. et al. *Drug Discov Today*, 2002, 7:1040-6; Gilmore, I. R. et al., *J. Drug Target.*, 2004, 12(6):315-340; Dykxhoorn, D. M. and Lieberman J., *Annu. Rev. Med.*, 2005, 56:401-423.

Systemic Delivery Using Liposomes:
 Lewis, D. L. et al. *Nat. Genet.*, 2002, 32:107-8; Paul, C. P. et al. *Nat. Biotechnol.*, 2002, 20:505-8; Song, E. et al. *Nat. Med.*, 2003, 9:347-51; Sorensen, D. R. et al. *J Mol Biol.*, 2003, 327:761-6.
Virus Mediated Transfer:
 Abbas-Terki, T. et al. *Hum Gene Ther.*, 2002, 13:2197-201; Barton, G. M. and Medzhitov, R. *Proc Natl Acad Sci USA*, 2002, 99:14943-5; Devroe, E. and Silver, P. A. *BMC Biotechnol.*, 2002, 2:15; Lori, F. et al. *Am J Pharmacogenomics*, 2002, 2:245-52; Matta, H. et al. *Cancer Biol Ther.*, 2003, 2:206-10; Qin, X. F. et al. *Proc Natl Acad Sci USA*, 2003, 100:183-8; Scherr, M. et al. *Cell Cycle*, 2003, 2:251-7; Shen, C. et al. *FEBS Lett.*, 2003, 539:111-4; Lee S. K. et al., *Blood*, 2005, 106(3):818-826, epub Apr. 14, 2005.
Peptide Delivery:
 Morris, M. C. et al. *Curr Opin Biotechnol.*, 2000, 11:461-6; Simeoni, F. et al. *Nucleic Acids Res.*, 2003, 31:2717-24.
 Song E. et al. describe antibody mediated in vivo delivery of siRNAs via cell-surface receptors (Song E. et al., *Nat. Biotechnol.*, 2005, 23(6):709-717, epub May 22, 2005).

Other technologies that may be suitable for delivery of polynucleotide viral inhibitors, such as interfering RNA, to the target cells are based on nanoparticles or nanocapsules such as those described in U.S. Pat. No. 6,649,192B and 5,843,509B. Recent technologies that may be employed for selecting, delivering, and monitoring interfering RNA molecules include Raab, R. M. and Stephanopoulos, G. *Biotechnol. Bioeng.*, 2004, 88:121-132; Huppi, K. et al. *Mol. Cell*, 2005, 17:1-10; Spagnou, S. et al. *Biochemistry*, 2004, 43:13348-13356; Muratovska, A. and Eccles, M. R. *FEBS Lett.*, 2004, 558:63-68; Kumar, R. et al. *Genome Res.*, 2003, 13:2333-2340; Chen, A. A. et al. *Nucleic Acids Res.*, 2005, 33:e190; Dykxhoorn, D. M. et al. *Gene Ther.*, 2006, epub ahead of print; Rodriguez-Lebron, E. and Paulson, H. L. *Gene Ther.*, 2005, epub ahead of print; Pai, S. I. et al. *Gene Ther.*, 2005, epub ahead of print; Raoul, C. et al. *Gene Ther.*, 2005, epub ahead of print; Manfredsson, F. P. et al. *Gene Ther.*, 2005, epub ahead of print; Downward, J. *BMJ*, 2004, 328:1245-1248.

A mixture of viral inhibitors, of the same type or different types, may be introduced into cells in vitro or in vivo. For example, a mixture or pool of polynucleotide viral inhibitors such as interfering RNA molecules (e.g., 2-4 interfering molecules or more) can be introduced into cells (Oleinikov A. V. et al., *Nucleic Acids Research*, 2005, 33(10):e92). Preferably, the interfering RNA molecules target different regions of the viral RNA. Preferably, the interfering RNA molecules have been previously validated as individually functioning to reduce viral load. The individual interfering RNAs of the mixture can be chemically synthesized (Elbashir S. M. et al., *Genes Dev.*, 2001, 15:188-200) or introduced as short DNA templates containing RNA polymerase promoter, which are transcribed within the cells in vitro or in vivo (Yu J. Y. et al., *Proc. Natl. Acad. Sci. USA*, 99:6047-6052).

Toxicity and therapeutic efficacy of compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices can be used. While compositions that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compositions generally lies within a range of circulating concentrations that include the ED50 with little or no toxicity. The dosage can vary within this range depending upon the dosage form employed and the route of administration utilized. For any composition used in the method of the invention, the therapeutically effective dose can be estimated initially from cell culture assays. A dose can be formulated in animal models to achieve a circulating plasma concentration range that includes the IC50 (i.e., the concentration of the test composition which achieves a half-maximal inhibition of symptoms) as determined in cell culture. Such information can be used to more accurately determine useful doses in humans. Levels in plasma can be measured, for example, by high performance liquid chromatography.

The viral inhibitors can be administered on any appropriate schedule, e.g., from one or more times per day to one or more times per week; including once every other day, for any number of days or weeks, e.g., 1 day, 2 days, 3 days, 4 days, 5 days, 6 days, 1 week, 10 days, 2 weeks, 3 weeks, 4 weeks, 5 weeks, 6 weeks, 7 weeks, 8 weeks, 2 months, 3 months, 6 months, or more, or any variation thereon. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a viral inhibitor can include a single treatment or can include a series of treatments.

The polynucleotide viral inhibitors can be introduced (administered) into cells (such as mammalian cells) in vitro or in vivo using known techniques, as those described herein, to suppress viruses. Similarly, genetic constructs (e.g., transcription vectors) containing DNA of the invention may be introduced into cells in vitro or in vivo using known techniques, as described herein, for transient or stable expression of RNA, to suppress viruses. When administered to the cells in vivo, the polynucleotide viral inhibitors can be administered to a subject systemically (e.g., intravenously).

As used herein, the terms "subject", "patient", and "individual" are used interchangeably and intended to include such human and non-human mammalian species. Likewise, in vitro methods of the present invention can be carried out on cells of such mammalian species. Host cells comprising exogenous polynucleotides of the invention may be administered to the subject, and may, for example, be autogenic (use of one's own cells), allogenic (from one person to another), or transgenic or xenogenic (from one mammalian species to another mammalian species), relative to the subject.

The polynucleotide viral inhibitors of the invention can be inserted into genetic constructs, e.g., viral vectors, retroviral vectors, expression cassettes, or plasmid viral vectors, e.g., using methods known in the art, including but not limited to those described in Xia et al., (2002), supra. Genetic constructs can be delivered to a subject by, for example, inhalation, orally, intravenous injection, local administration (see U.S. Pat. No. 5,328,470) or by stereotactic injection (see, e.g., Chen et al., *Proc. Natl. Acad. Sci. USA* 91:3054-3057 (1994)). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the polynucleotide delivery system.

The polynucleotide viral inhibitors can be small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides (Brummelkamp et al., *Science* 296:550-553 (2002); Lee et al., (2002), supra; Miyagishi and Taira, *Nature Biotechnol.* 20:497-500 (2002); Paddison et al. (2002), supra; Paul (2002), supra; Sui (2002) supra; Yu et al. (2002), supra.

siRNAs targeting viruses may be fused to other nucleotide molecules, or to polypeptides, in order to direct their delivery or to accomplish other functions. Thus, for example, fusion proteins comprising a siRNA oligonucleotide that is capable of specifically interfering with target viruses may comprise affinity tag polypeptide sequences, which refers to polypeptides or peptides that facilitate detection and isolation of the polypeptide via a specific affinity interaction with a ligand. The ligand may be any molecule, receptor, counter-receptor, antibody or the like with which the affinity tag may interact through a specific binding interaction as provided herein. Such peptides include, for example, poly-His or "FLAG" or the like, e.g., the antigenic identification peptides described in U.S. Pat. No. 5,011,912 and in Hopp et al., (*Bio/Technology* 6:1204, 1988), or the XPRESS epitope tag (INVITROGEN, Carlsbad, Calif.). The affinity sequence may be a hexa-histidine tag as supplied, for example, by a pBAD/His (INVITROGEN) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., 1984 *Cell* 37:767).

The present invention also relates to vectors and to constructs that include or encode polynucleotide viral inhibitors (e.g., siRNA), and in particular to "recombinant nucleic acid constructs" that include any nucleic acid such as a DNA polynucleotide segment that may be transcribed to yield antiviral siRNA polynucleotides according to the invention as provided herein; to host cells which are genetically engineered with vectors and/or constructs of the invention and to the production of siRNA polynucleotides, polypeptides, and/or fusion proteins of the invention, or fragments or variants thereof, by recombinant techniques. siRNA sequences disclosed herein as RNA polynucleotides may be engineered to produce corresponding DNA sequences using well-established methodologies such as those described herein. Thus, for example, a DNA polynucleotide may be generated from any siRNA sequence described herein, such that the present siRNA sequences will be recognized as also providing corresponding DNA polynucleotides (and their complements). These DNA polynucleotides are therefore encompassed within the contemplated invention, for example, to be incorporated into the subject invention recombinant nucleic acid constructs from which siRNA may be transcribed.

According to the present invention, a vector may comprise a recombinant nucleic acid construct containing one or more promoters for transcription of an RNA molecule, for example, the human U6 snRNA promoter (see, e.g., Miyagishi et al., *Nat. Biotechnol.* 20:497-500 (2002); Lee et al., *Nat.*

*Biotechnol.* 20:500-505 (2002); Paul et al., *Nat. Biotechnol.* 20:505-508 (2002); Grabarek et al., *BioTechniques* 34:73544 (2003); see also Sui et al., *Proc. Natl. Acad. Sci. USA* 99:5515-20 (2002)). Each strand of a siRNA polynucleotide may be transcribed separately each under the direction of a separate promoter and then may hybridize within the cell to form the siRNA polynucleotide duplex. Each strand may also be transcribed from separate vectors (see Lee et al., supra). Alternatively, the sense and antisense sequences specific for a target viral sequence may be transcribed under the control of a single promoter such that the siRNA polynucleotide forms a hairpin molecule (Paul et al., supra). In such instance, the complementary strands of the siRNA specific sequences are separated by a spacer that comprises at least four nucleotides, but may comprise at least 5, 6, 7, 8, 9, 10, 11, 12, 14, 16, or 18 or more nucleotides as described herein. In addition, siRNAs transcribed under the control of a U6 promoter that form a hairpin may have a stretch of about four uridines at the 3' end that act as the transcription termination signal (Miyagishi et al., supra; Paul et al., supra). By way of illustration, if the target sequence is 19 nucleotides, the siRNA hairpin polynucleotide (beginning at the 5' end) has a 19-nucleotide sense sequence followed by a spacer (which as two uridine nucleotides adjacent to the 3' end of the 19-nucleotide sense sequence), and the spacer is linked to a 19 nucleotide antisense sequence followed by a 4-uridine terminator sequence, which results in an overhang. siRNA polynucleotides with such overhangs effectively interfere with expression of the target polypeptide. A recombinant construct may also be prepared using another RNA polymerase III promoter, the H1 RNA promoter, that may be operatively linked to siRNA polynucleotide specific sequences, which may be used for transcription of hairpin structures comprising the siRNA specific sequences or separate transcription of each strand of a siRNA duplex polynucleotide (see, e.g., Brummelkamp et al., *Science* 296:550-53 (2002); Paddison et al., supra). DNA vectors useful for insertion of sequences for transcription of an siRNA polynucleotide include pSUPER vector (see, e.g., Brummelkamp et al., supra); pAV vectors derived from pCWRSVN (see, e.g., Paul et al., supra); and pIND (see, e.g., Lee et al., supra), or the like.

Polynucleotide viral inhibitors can be expressed in mammalian cells, yeast, bacteria, or other cells under the control of appropriate promoters, providing ready systems for evaluation of siRNA polynucleotides that are capable of suppressing viral load as provided herein. Appropriate cloning and expression vectors for use with prokaryotic and eukaryotic hosts are described, for example, by Sambrook, et al., Molecular Cloning: A Laboratory Manual, Third Edition, Cold Spring Harbor Laboratory Press, N.Y., (2001).

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 Current Protocols in Molecular Biology, Greene Publ. Assoc. Inc. & John Wiley & Sons, Inc., Boston, Mass.); Sambrook et al. (2001 Molecular Cloning, Third Ed., Cold Spring Harbor Laboratory, Plainview, N.Y.); Maniatis et al. (1982 Molecular Cloning, Cold Spring Harbor Laboratory, Plainview, N.Y.); and elsewhere.

The DNA sequence in the expression vector is operatively linked to at least one appropriate expression control sequence (e.g., a promoter or a regulated promoter) to direct mRNA synthesis. Representative examples of such expression control sequences include LTR or SV40 promoter, the *E. coli* lac or trp, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Examples of Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a polynucleotide of the invention is described herein.

As noted above, in certain embodiments the vector may be a viral vector such as a mammalian viral vector (e.g., retrovirus, adenovirus, adeno-associated virus, lentivirus). For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters which may be employed include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and beta-actin promoters). Other viral promoters that may be employed include, but are not limited to, adenovirus promoters, adeno-associated virus promoters, thymidine kinase (TK) promoters, and B19 parvovirus promoters. The selection of a suitable promoter will be apparent to those skilled in the art from the teachings contained herein, and may be from among either regulated promoters (e.g., tissue-specific or inducible promoters) or promoters as described above).

In another aspect, the present invention relates to host cells containing the above described recombinant constructs. Host cells are genetically engineered/modified (transduced, transformed or transfected) with the vectors and/or expression constructs of this invention that may be, for example, a cloning vector, a shuttle vector, or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding siRNA polynucleotides or fusion proteins thereof. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or 293 cells; adenoviruses; plant cells, or any suitable cell already adapted to in vitro propagation or so established de novo.

Various mammalian cell culture systems can also be employed to produce polynucleotide viral inhibitors from recombinant nucleic acid constructs of the present invention. The invention is therefore directed in part to a method of producing a polynucleotide, such as an siRNA, by culturing a host cell comprising a recombinant nucleic acid construct that comprises at least one promoter operably linked to a polynucleotide viral inhibitor. In certain embodiments, the promoter may be a regulated promoter as provided herein, for example a tetracycline-repressible promoter. In certain embodiments the recombinant expression construct is a recombinant viral expression construct as provided herein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa, HEK, and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of recombinant polynucleotide constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, liposomes including cationic liposomes, calcium phosphate transfection, DEAE-Dextran mediated transfection, or electroporation (Davis et al., 1986 Basic Methods in Molecular Biology), or other suitable technique.

The expressed polynucleotides may be useful in intact host cells; in intact organelles such as cell membranes, intracellular vesicles or other cellular organelles; or in disrupted cell preparations including but not limited to cell homogenates or lysates, microsomes, uni- and multilamellar membrane vesicles or other preparations. Alternatively, expressed polynucleotides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Finally, high performance liquid chromatography (HPLC) can be employed for final purification steps.

As used herein, the terms "administer", "introduce", "apply", "treat", "transplant", "implant", "deliver", and grammatical variations thereof, are used interchangeably to provide viral inhibitors to target cells in vitro (e.g., ex vivo) or in vivo, or provide genetically modified (engineered) cells of the subject invention to a subject.

As used herein, the term "co-administration" and variations thereof refers to the administration of two or more agents simultaneously (in one or more preparations), or consecutively. For example, one or more types of genetically modified cells of the invention can be co-administered with other agents.

Viral inhibitors (also referred to herein as "active compounds") can be incorporated into pharmaceutical compositions suitable for administration. Such compositions typically comprise the virus-inhibiting nucleic acid molecule and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to target cells with monoclonal antibodies) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Assays.

The invention also provides a method (also referred to herein as a "screening assay") for identifying viral inhibitors, i.e., candidate or test compounds or agents that have an inhibitory effect on, for example, the viral proliferation, especially H5N1.

Methods of Treatment.

The present invention provides for both prophylactic and therapeutic methods of treating a subject at risk of (or susceptible to) a viral infection.

Prophylactic Methods.

In one aspect, the invention provides a method for preventing in a subject, a disease or condition associated with viral infection by administering to the subject an agent which delivers an effective amount of the subject siRNAs.

Therapeutic Methods.

Another aspect of the invention pertains to methods of modulating the viral activity for therapeutic purposes. The modulation of expression of the target gene disclosed in the method of the invention involves contacting a cell with an agent that delivers an effective amount of the subject siRNAs to the targeted cell. As such, the present invention provides methods of treating an individual afflicted with a disease or disorder characterized by viral infection.

The dosage ranges for the administration of the therapeutic agents of the invention are those large enough to produce the desired effect in which the symptoms of viral infection are treated. The dosage should not be so large as to cause adverse side effects, such as unwanted cross-reactions, anaphylactic reactions, and the like. Generally, the dosage will vary with the age, condition, sex and extent of the symptoms in the patient and can be determined by one of skill in the art. The dosage can be adjusted by the individual physician in the event of any counterindications. The dosage amount may depend on the virus which is treated and can be readily determined using known dosage adjustment techniques by a physician having ordinary skill in treatment of these disorders. The dosage amount will generally lie within an established therapeutic window for the therapeutic compound which will provide a therapeutic effect while minimizing additional morbidity and mortality. Typically, therapeutic compounds will be administered in a dosage ranging from 0.001 mg/kg to about 100 mg/kg per dose, preferably 0.1-20 mg/kg. The preferred dose of about 0.5-5 mg/kg is particularly useful for compounds containing the therapeutic agents disclosed herein, in one or more dose administrations daily, for one or several days.

Any of the compositions described herein may be formulated for pharmacological or therapeutic administration either to a mammal, or more preferably to a human. As such, the compositions may be contained in a pharmaceutically acceptable carrier. The preferred mode of administration of a peptide active agent is by injection, either intravenous, intraarterial, intramuscular or subcutaneous. Other routes of administration may also be possible and would be included within the scope of the present disclosure.

The compositions may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The therapeutic agents of the invention can be administered parenterally by injection or by gradual perfusion over time. The therapeutic agents of the invention can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

The invention also relates to a method for preparing a medicament or pharmaceutical composition comprising the therapeutic agents of the invention, the pharmaceutical composition being used for therapy of viral infection.

In certain embodiments of the invention, the viruses are targets for molecular therapy. For this, the application of small interfering RNA (siRNA) as viral antagonists can be used to inhibit or downregulate the viral proliferation.

By "inhibit", "downregulate", "knockdown" or "silence" it is meant that the expression of the targeted viral RNAs is reduced below that observed in the absence of the siRNAs of the invention. In an embodiment, inhibition or downregulation of H5N1 with the siRNAs-m of the instant invention is greater in the presence of the siRNAs-m than in its absence.

This invention relates to compounds, compositions, and methods useful for modulating viral proliferation, such as H5N1, using short interfering nucleic acid (siNA) molecules. This invention further relates to compounds, compositions, and methods useful for modulating the expression and activity of H5N1 and/or H5N1 genes by RNA interference (RNAi) using small nucleic acid molecules. In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the proliferation of viruses, and especially H5N1. A siRNA of the invention can be unmodified or chemically-modified. A siRNA of the instant invention can be chemically synthesized, expressed from a vector or enzymatically synthesized. The instant invention may also feature various chemically-modified synthetic short interfering nucleic acid (siNA) molecules capable of modulating viral proliferation, such as H5N1, in cells by RNA interference (RNAi). The use of chemically-modified siNA improves various properties of native siNA molecules through increased resistance to nuclease degradation in vivo and/or through improved cellular uptake. The siNA molecules of the instant invention provide useful reagents and methods for a variety of therapeutic, diagnostic, target validation, genomic discovery, genetic engineering, and pharmacogenomic applications.

In one embodiment, the invention features a medicament comprising a siRNA molecule of the invention.

In one embodiment, the invention features an active ingredient comprising a siRNA molecule of the invention.

In one embodiment, the invention features a composition comprising a siRNA molecule of the invention in a pharmaceutically acceptable carrier or diluent.

It should be understood, however, that this invention is not limited to the particular embodiments described, as such may, of course, vary. It is also to be understood that the terminology used herein is for the purpose of describing particular embodiments only, and is not intended to be limiting.

As used in this specification, including the appended claims, the singular "a", "an", and "the" include plural reference unless the contact dictates otherwise. Thus, for example, a reference to "a polynucleotide" includes more than one such polynucleotide. A reference to "a nucleic acid sequence" includes more than one such sequence. A reference to "a cell" includes more than one such cell.

The terms "comprising", "consisting of" and "consisting essentially of" are defined according to their standard meaning. The terms may be substituted for one another throughout the instant application in order to attach the specific meaning associated with each term.

Unless defined otherwise, all technical and scientific terms have the same meaning as commonly understood by one of ordinary skill in the art to which this invention belongs. Although any methods and materials similar or equivalent to those described herein can be used in the practice or testing of the present invention, the preferred methods and materials are now described.

Figure 4J:
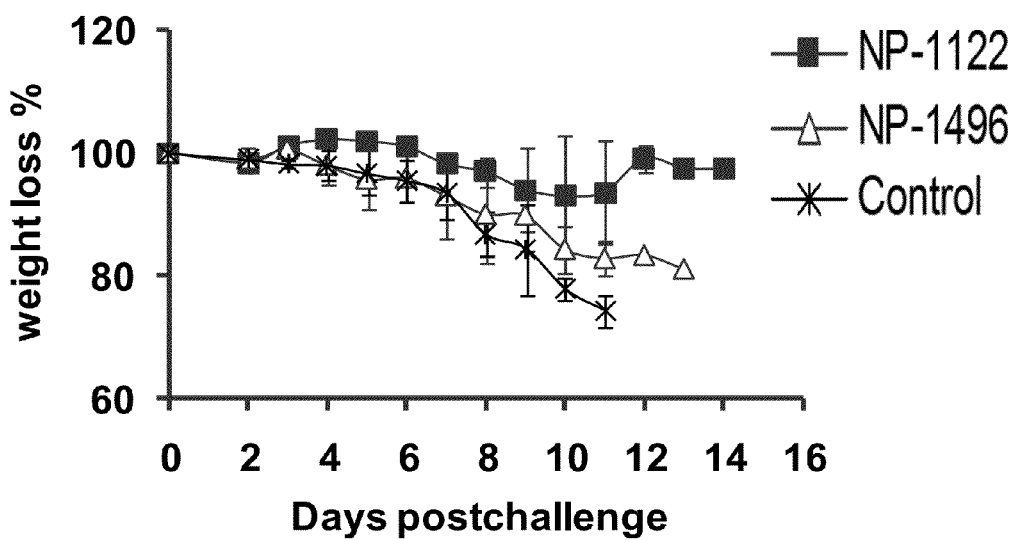
Figure 5A:
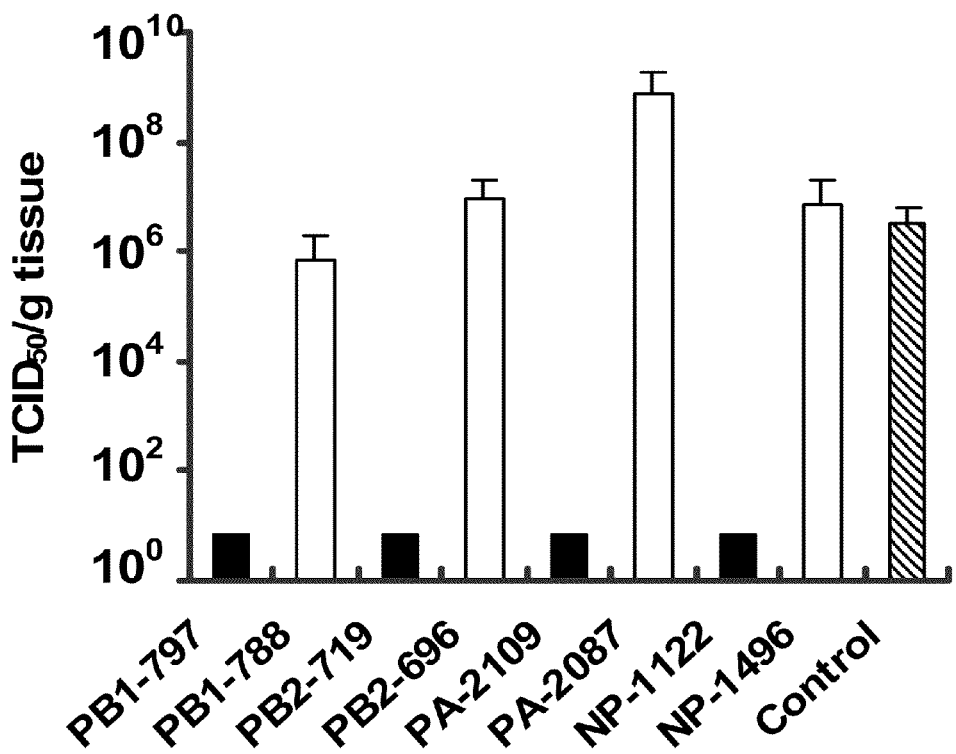
FIG. 5 represents detection of viral replication and tissue damage in lungs of mice treated with siRNAs-m and siRNAs-n. Lung tissues were obtained from mice treated with siRNAs-m (black) or siRNAs-n (white) on 6th day post-challenge. Control mice (control) were given PEGS-PEI1.8. (a) Detection of viral titers in mouse lung tissues. Virus titers in lung samples were determined by $TCID_{50}$. The detection limit is 1:10 which is indicated with a dashed line. (b) Detection of viral RNA copies in mouse lung tissues. Viral RNA copies were measured by real-time RT-PCR. (c) Detection of histopathological changes in lung tissues. Representative histological sections of the lung tissues were stained with H&E (original magnification 100×). Inflammatory infiltrate and alveolar damage are seen as thickening of the alveolar septum with some obliteration of alveolar space at this magnification.
Figure 5B:
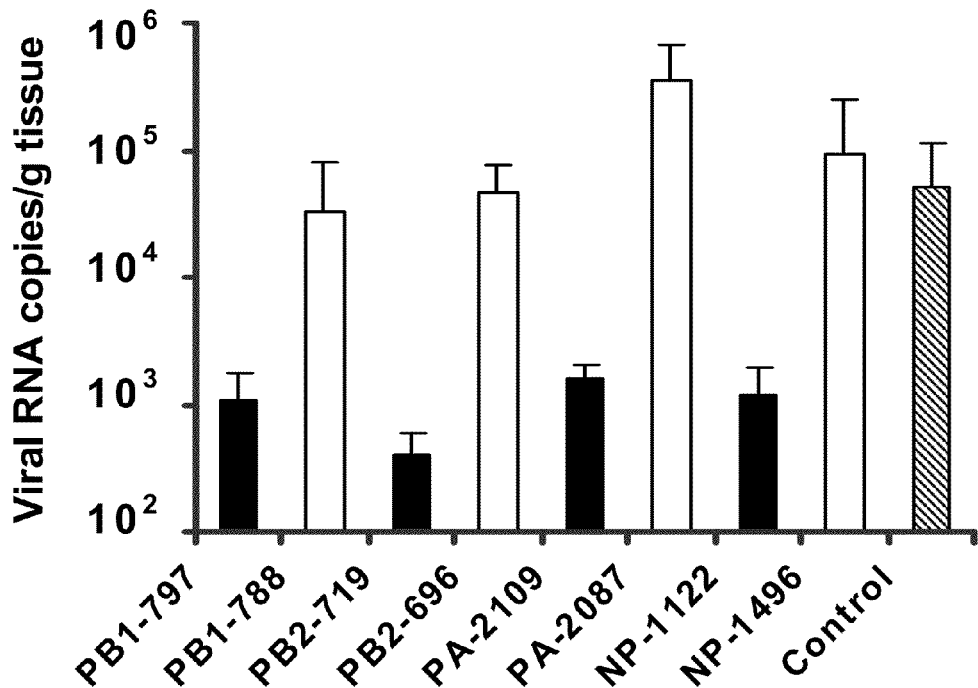
Figure 5C:
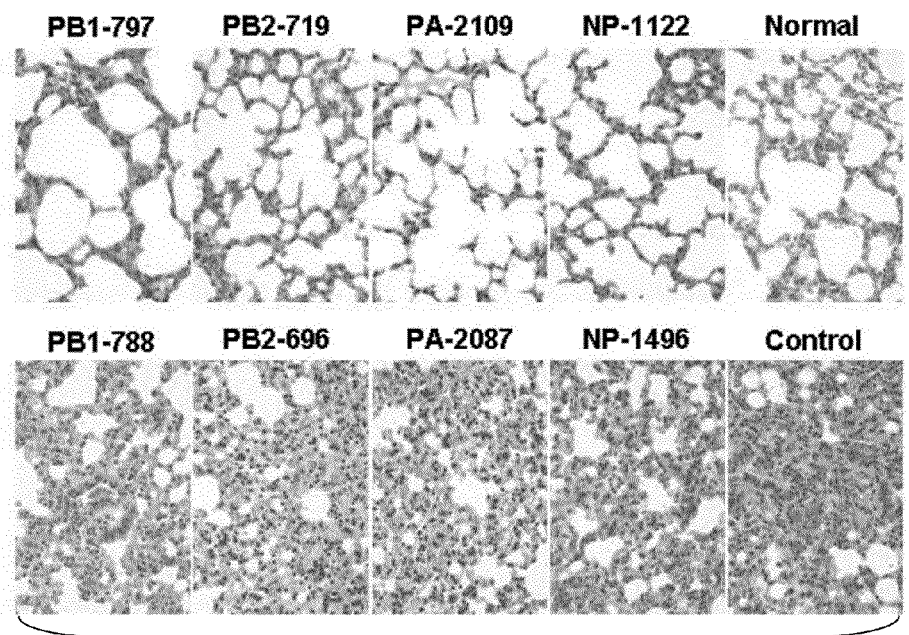
Figure 6C:
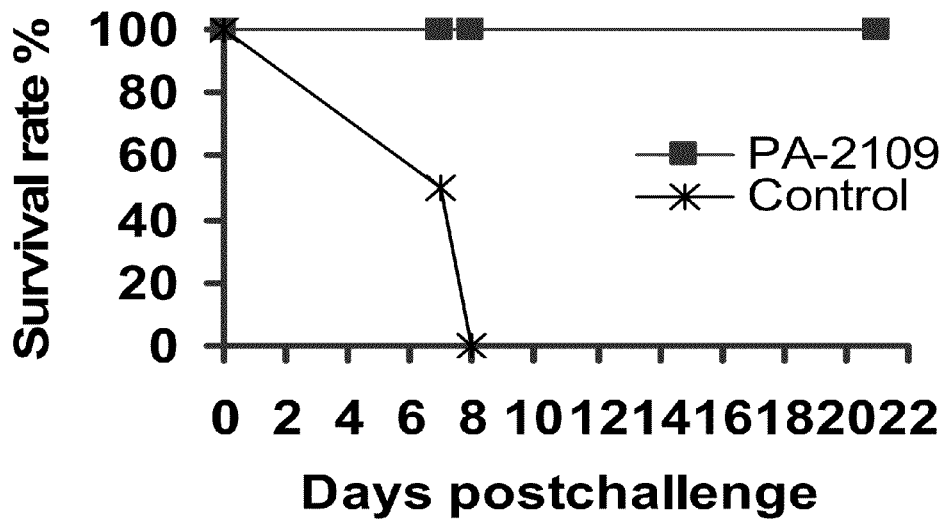
Figure 6D:
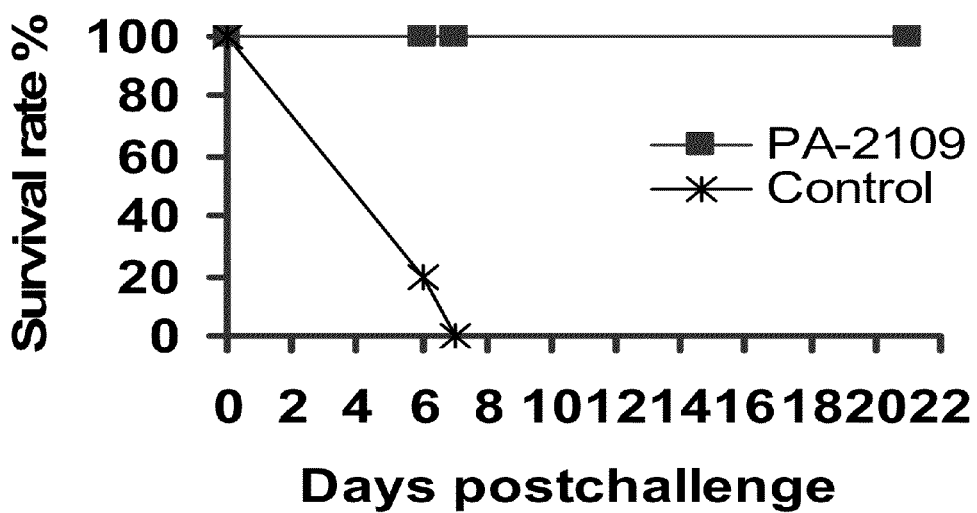

The excellent in vivo antiviral effect of the siRNAs-m taught herein can be mainly attributed to unique features of the identified motif. First, the siRNAs-m, particularly PB 1-797 which shares 10 overlapping nt residues with its siRNA-n counterpart, showed much lower effect than their corresponding siRNAs-n in inhibiting viral replication in cultured cells (FIG. 3a). In sharp contrast, they exhibited significantly higher antiviral effects than their siRNA-n counterparts in animals (FIGS. 4 & 5). Second, the siRNAs-m showed low cross-strain antiviral effect in cultured cells (FIG. 6b), but demonstrated full cross-protection against two imperfectly matched H5N1 virus strains in vivo (FIG. 6c & d). Third, a small RNA containing the motif, which is considered suboptimal according to generally accepted criteria and cannot be identified using siRNA target designer program from Promega, did not display any antiviral effect in cultured cells, but exhibited more pronounced in vivo antiviral effect than most siRNAs-n (FIGS. 4 & 6g), which showed very high antiviral activity in cultured cells (FIG. 3a). This indicates that, besides the siRNA-mediated antiviral activity, the motif itself can stimulate the host to generate a stronger antiviral effect.

Figure 7A:
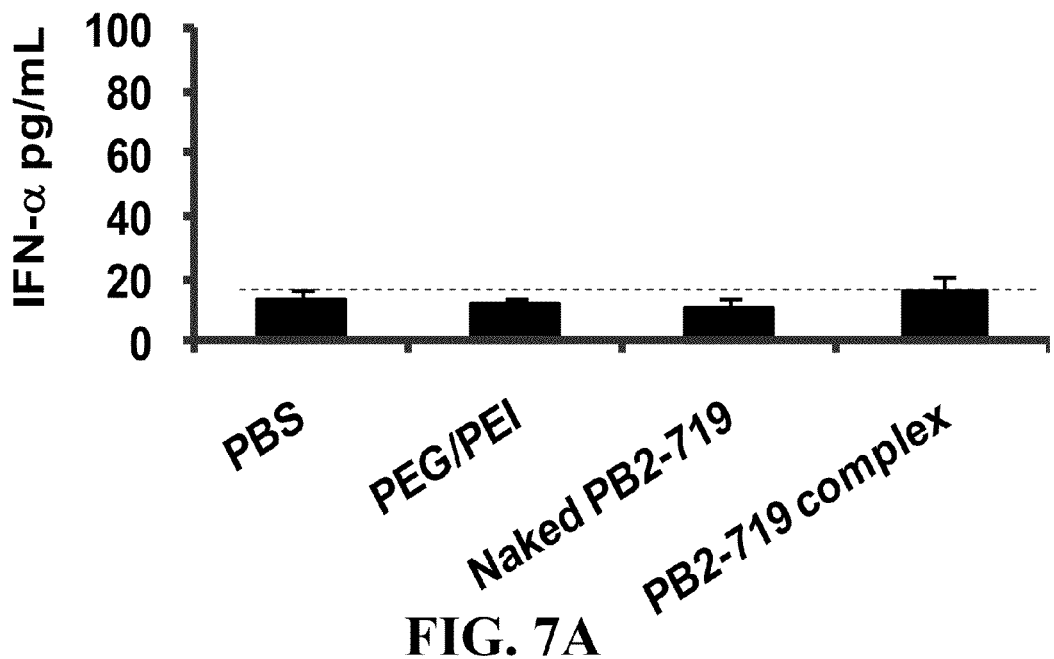
FIG. 7 graphically depicts detection of innate immune responses stimulated by siRNAs-m in lung tissues. (a) Detection of IFN-α response. (b) Detection of IFN-γ response. (c) Detection of TNF-α response. (d) Detection of IL-6 response. (e) Detection of IL-6 response at different time-points. (f) Detection of IL-6 response in mice receiving different doses of siRNA-m. (g) Detection of IL-6 response in mice treated with sense and antisense strands of siRNA-m. (h) Detection of IL-6 response in mice treated with another siRNA-m (PA-2109). Mice were i.t administered one dose of 100 µg or indicated amounts of siRNA-m (PB2-719) or the indicated siRNAs and their controls. Lung samples were collected at 7 h or indicated time-points post-treatment. The indicated cytokines in lung samples were detected by ELISA. Detection limits of these cytokines are indicated with a dashed line. ** $P<0.005$ compared with other treatments, * $P<0.05$ compared with other treatments.
Figure 7B:
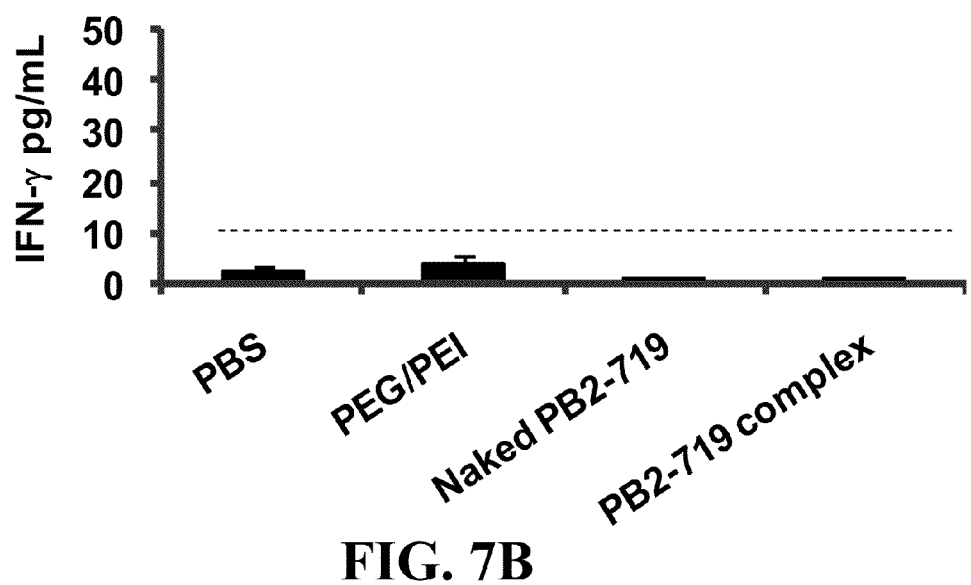
Figure 7C:
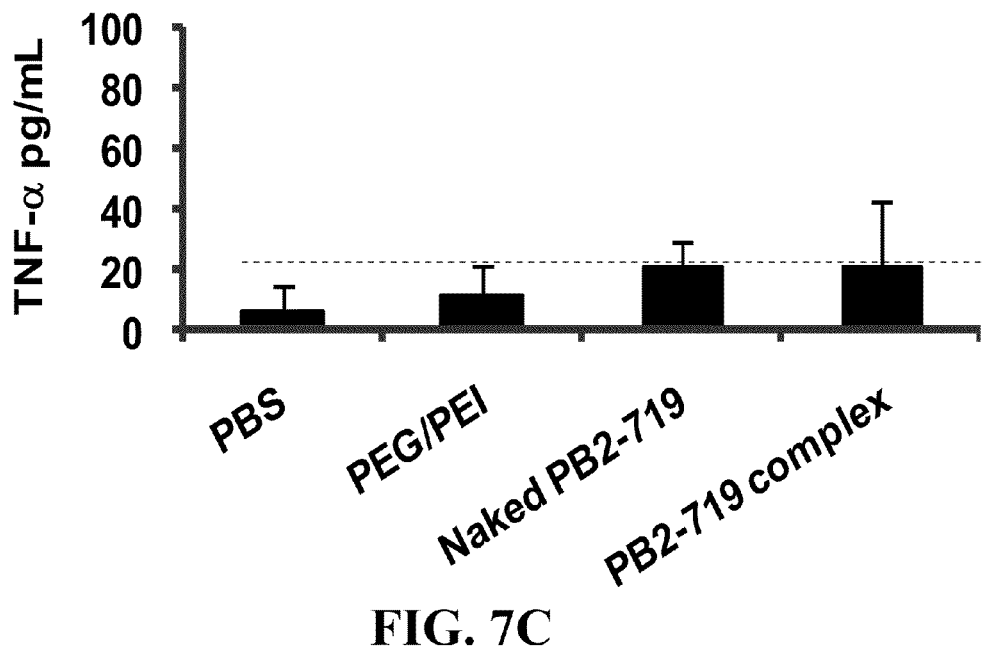
Figure 7D:
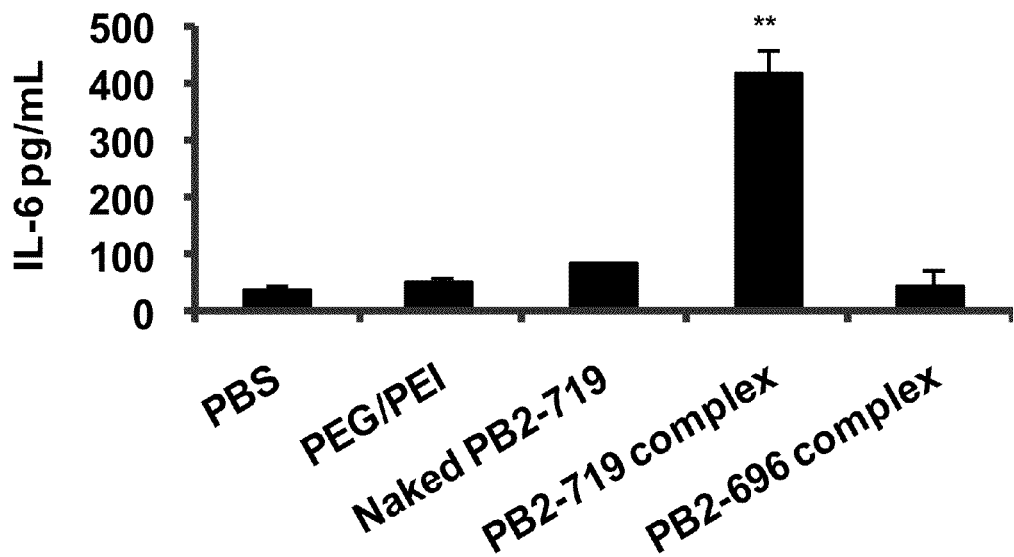
Figure 7E:
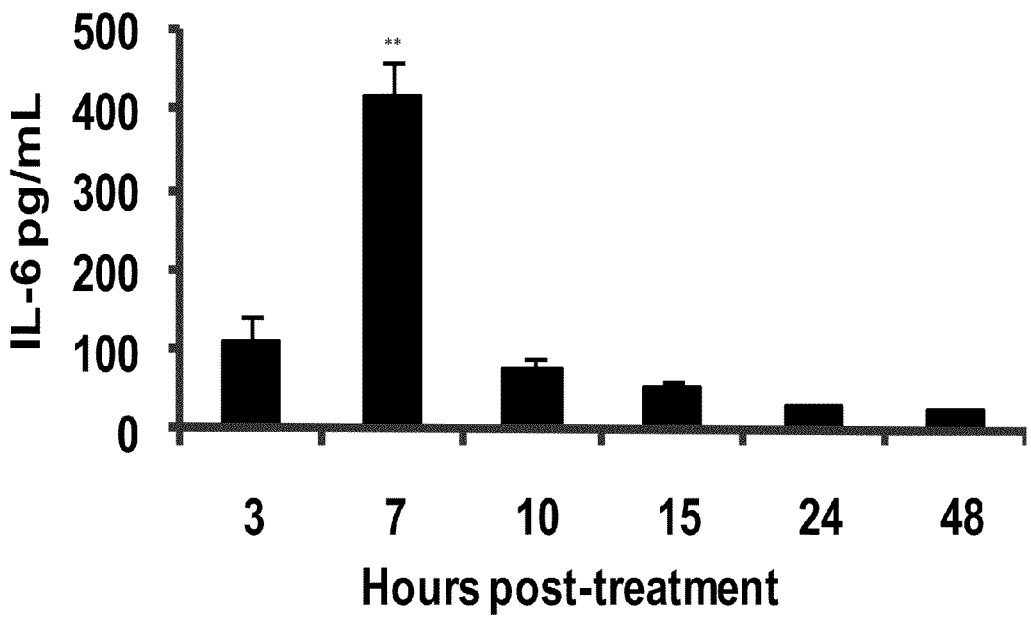
Figure 7F:
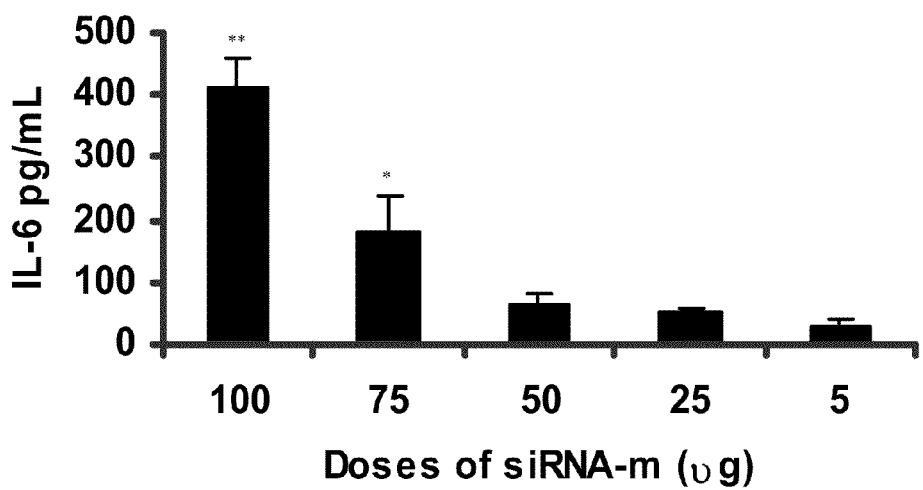
Figure 7G:
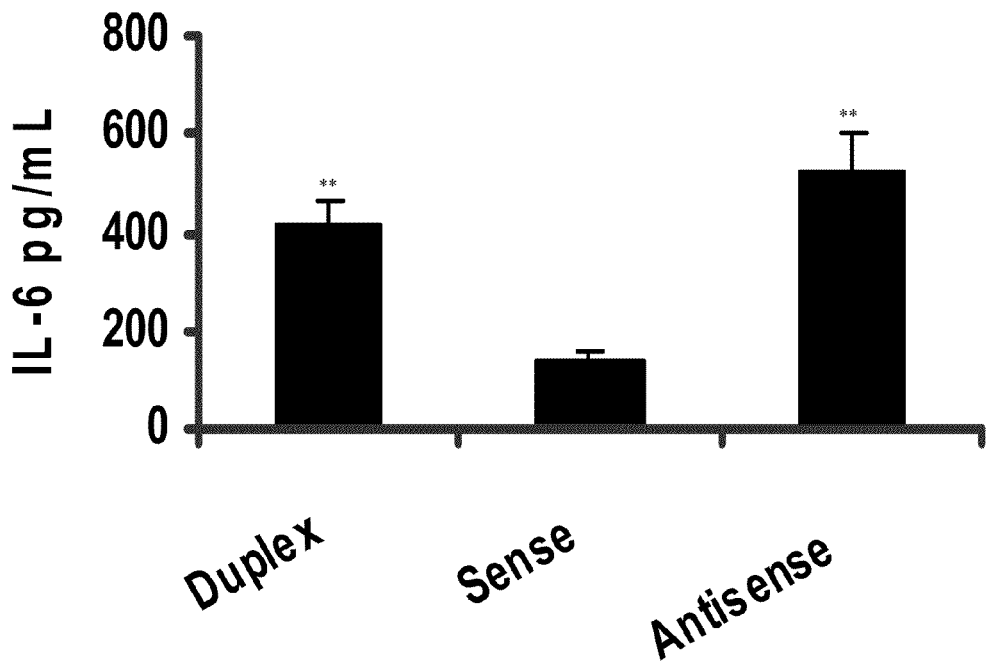

The underlying mechanism by which siRNAs-m potently protect animal models from lethal challenge of the highly virulent H5N1 virus is not fully known. However, siRNAs-m identified herein are different from the other reported siRNAs that can stimulate the mammalian innate immune responses in a sequence dependent and independent manner[14-16,20,21], since our results did not show any IFN-α, IFN-γ and TNF-α production in response to the treatment of siRNAs-m in mouse serum samples or lung homogenates collected from different time-points (FIG. 2 and FIGS. 7a, b & c). Interestingly, siRNAs-m stimulated local IL-6 production in the acute phase in lungs (FIGS. 7d to f). Further analysis revealed that the antisense sequence of the motif, 5'-GGAGU-3', was associated with the stimulation of IL-6 generation (FIG. 7g). This is a novel sequence motif identified in this study, which is different from the previously reported siRNA motifs, such as 5'-UGUGU-3' and 5'-GUCCUUCAA-3'$_{(15,16)}$. Although it has been reported that local IL-6 production induced by viral infection is associated with acute lung injury and the severity of influenza virus infection$_{(22,23)}$, several studies have found that local IL-6 production is associated with up-regulation of the immune defense system of the epithelial cells$_{(24-29)}$. More direct antiviral activity mediated by IL-6 has also been reported to be associated with the induction of proteins and enzymes that can inhibit viral replication by impairing accumulation of viral-specific mRNAs, double-stranded RNAs, and proteins$_{(30)}$. Regardless of whether siRNA-m induced IL-6 generation is directly or indirectly associated with in vivo antiviral activity of siRNAs-m, our results indicated that IL-6 production was protective in the host defense against H5N1 virus infection.

Figure 8A:
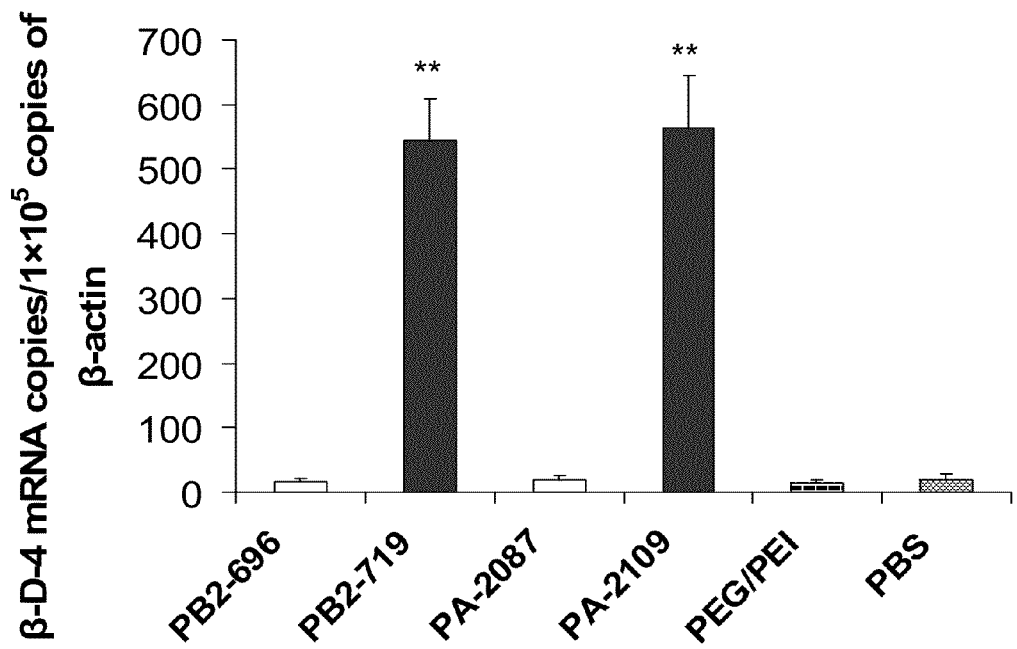
FIG. 8 graphically depicts detection of β-defensin-4 responses stimulated by siRNAs-m in lung tissues. (a) Detection of β-defensin-4 (β-D-4) response stimulated by siRNAs-m (PB2-719 and PA-2109) and siRNAs-n (PB2-696 and PA-2087). (b) Detection of β-D-4 response in mice treated with sense and antisense strands of siRNA-m (PB2-719). (c) Detection of β-D-4 response at different time-points. (d) Detection of β-D-4 response in mice given different doses of siRNA-m (PB2-719). (e) Detection of β-D-4 productions in lung tissues of mice treated with siRNAs-m (PB2-719 and PA-2109) and siRNAs-n (PB2-696 and PA-2087). Representative histological sections of the lung tissues were stained with antiserum of rabbit immunized by synthetic β-D-4 peptide or normal rabbit serum (unstained) (original magnification 100×). Mice were i.t administered one dose of 100 µg or indicated amounts of siRNAs-m or the indicated siRNAs-n and their controls (PEG/PEI and PBS). Lung samples were collected at 7 h or indicated time-points post-treatment. ** $P<0.005$ compared with other treatments, * $P<0.05$ compared with other treatments.
Figure 8B:
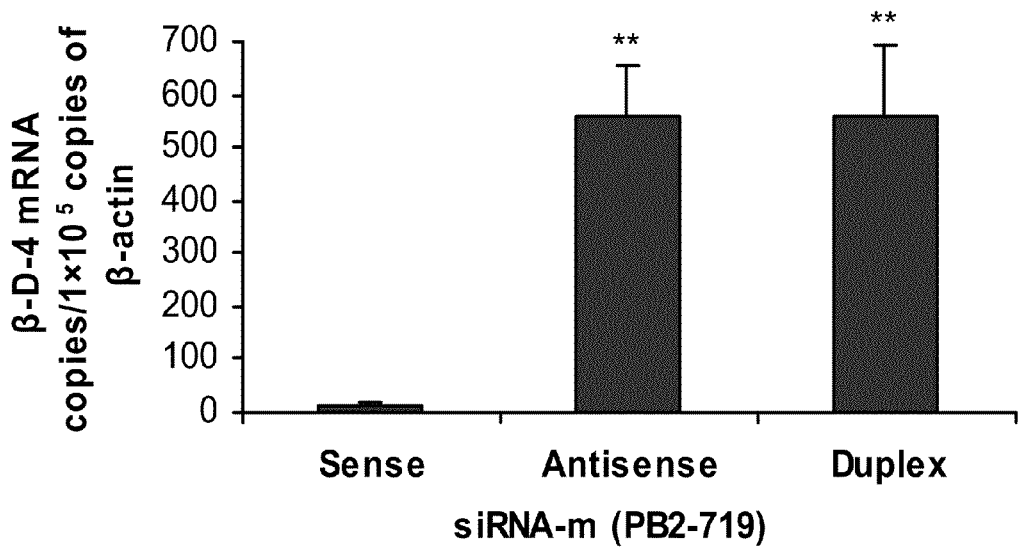
Figure 8C:
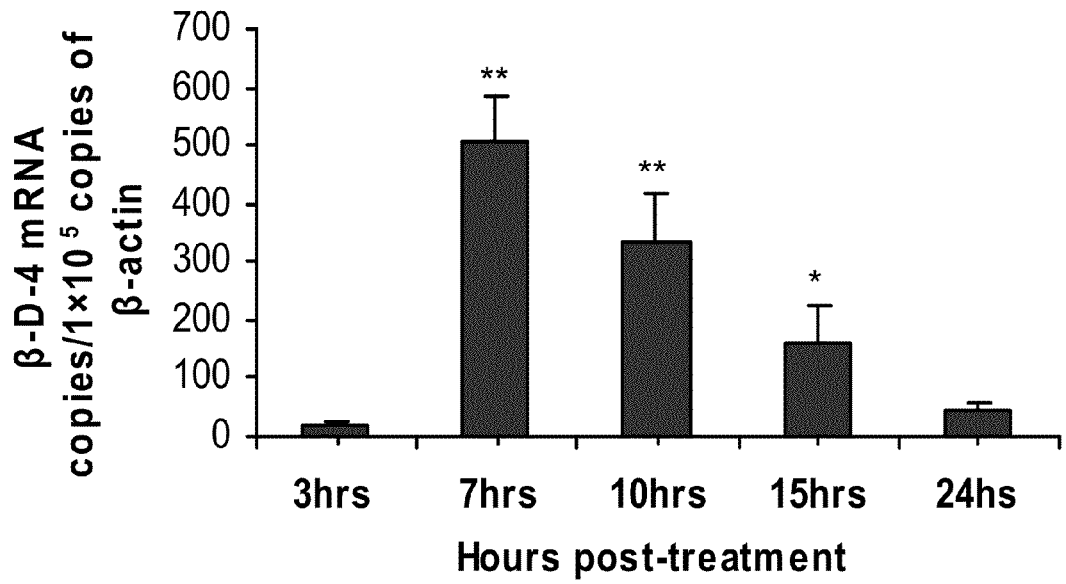
Figure 8D:
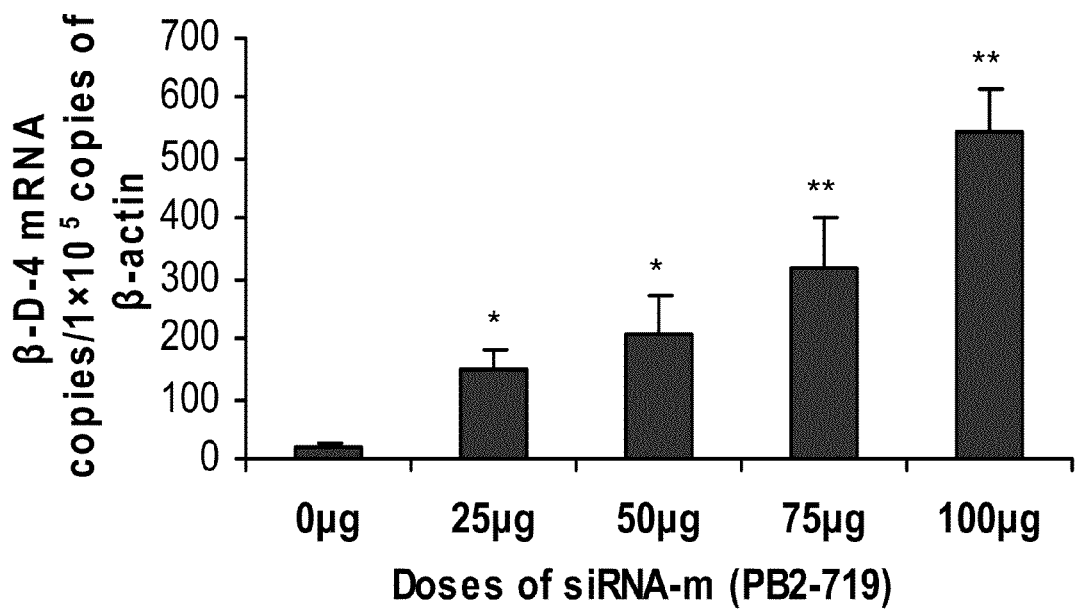
Figure 8E:
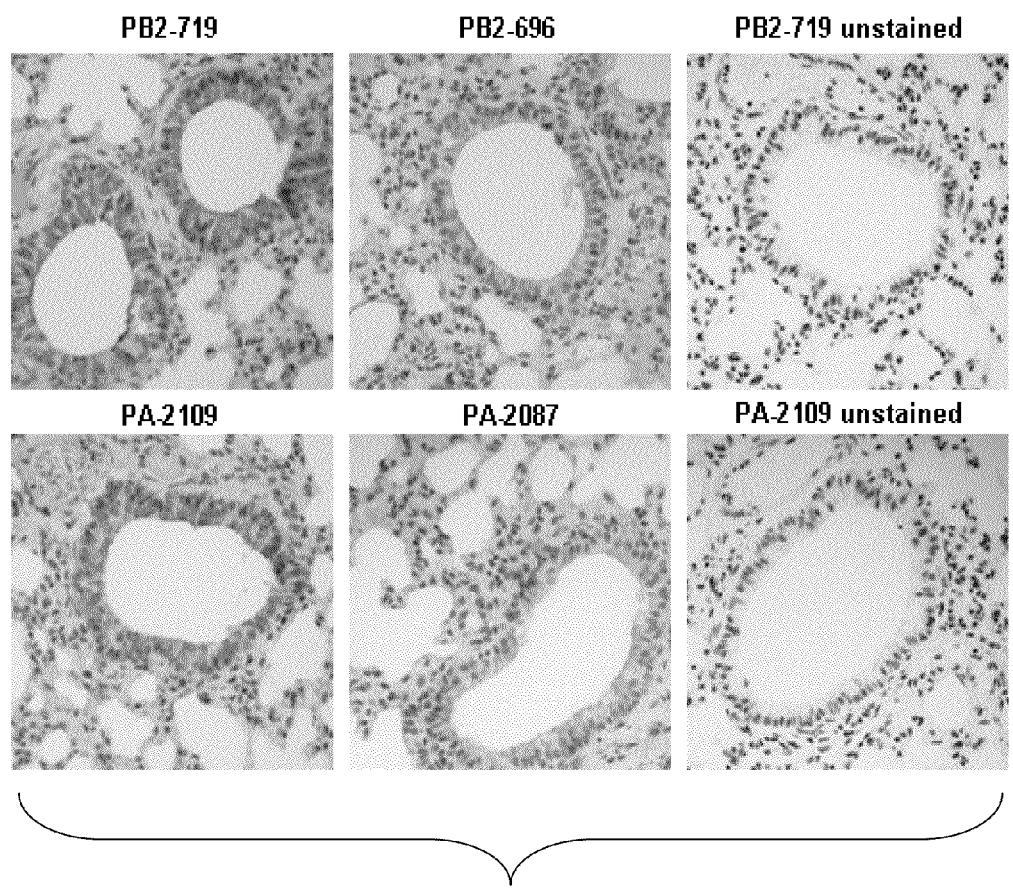

Our results further showed that siRNAs-m stimulated high level of local β-defensin-4 production in lung tissues of the mice (FIGS. 8a and b), reaching the highest level as early as 7 hours post-treatment (FIG. 8c). The β-defensin-4 generation was dose dependent (FIG. 8d). Immunostaining of lung tissues using β-defensin-4 specific antibody revealed that siRNA-m stimulated β-defensin-4 is mainly expressed in epithelial cells of tracheal mucous membrane; it is rarely found in aveleo tissues (FIG. 8e). The stimulation of β-defensin-4 in mouse lungs by siRNAs-m was confirmed in both mRNA and protein levels.

In addition, it has been found that β-defensins provide a first line of host defense against various infectious pathogens, such as bacteria, fungi and some enveloped viruses$_{(33)}$. Importantly, β-defensin can also function as a bridge between innate and adaptive immunity$_{(34)}$. For example, β-defensin acts directly on immature dendritic cells as a ligand for Toll-like receptor-4, thereby promoting the maturation of dentritic cells$_{(35)}$. For another example, human β-defensin-2 has been found to play an important role in the innate immunity and host defense responses in lungs of human$_{(36)}$. It has also been reported that mouse β-defensin-4, a homologue of human β-defensin-2, can be induced by *Mycobacterium tuberculosis* and influenza A virus infections in animal models and act as innate immunity against the infections$_{(37, 38)}$. However, whether siRNAs-m induced β-defensin-4 has anti-H5N1 activity has not been evaluated yet.

Figure 9A:
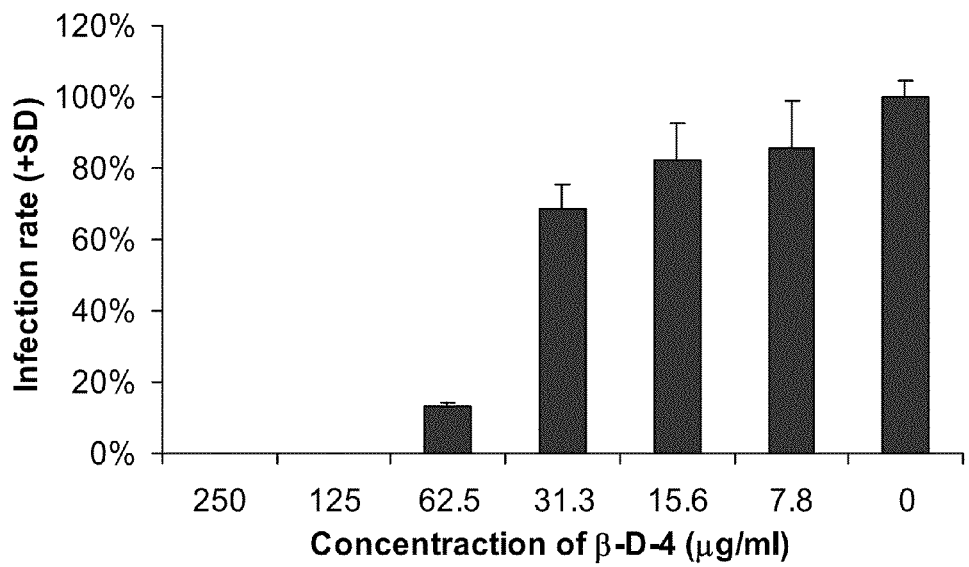
FIG. 9 graphically depicts evaluation of ex vivo and in vivo antiviral effects of β-defensin-4. (a) Evaluation of ex vivo antiviral effects of β-defensin-4 (β-D-4) in cell cultures. Indicated concentrations of β-D-4 were added to MDCK cells, which are then infected with 100 $TCID_{50}$ of H5N1 A/Vietnam/1194/04 strain for 48 h. Cell supernatants were collected for plaque assay to detect the released virus titers. Infection rate was defined as virus titers of β-D-4 treated cell cultures compared to that of untreated cell cultures. (b) Evaluation of in vivo antiviral effects of β-D-4 in H5N1 virus infected mouse model. Mice were i.n. administered one dose of 75 µg β-D-4 or control protein and then challenged with 10 $LD_{50}$ of H5N1 A/Vietnam/1194/04 strain. Survival, body weight and general conditions were monitored for 21 days or until death.
Figure 9B:
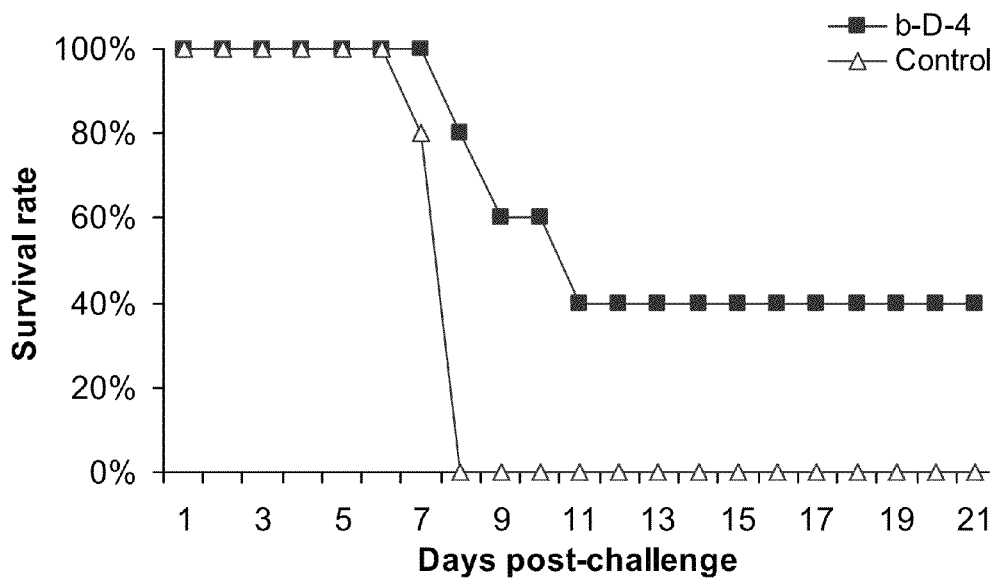

To examine the anti-H5N1 activity of siRNAs-m induced β-defensin-4 in ex vivo and in vivo systems, β-defensin-4 was cloned and expressed. In ex vivo systems, β-defensin-4 showed strong anti-H5N1 activity with IC50 at around 45 μg/ml level (FIG. 9a). In in vivo systems, one dose of 75 μg β-defensin-4 could protect 40% mice from lethal challenge of H5N1 virus. Even for those mice that are treated with β-defensin-4 but fail to survive, they are able to live 2 days longer than controls (FIG. 9b). These results, show that the potent anti-H5N1 effects of siRNAs-m can be attributed to, at least in part, the novel motif stimulating a strong β-defensin response, which plays an important role in protecting the host against highly pathogenic H5N1 virus infection.

We have thus demonstrated that siRNAs containing a novel motif have greatly enhanced anti-H5N1 activity in vivo. This motif is distinct from previously-reported siRNA-related motifs. The other motifs usually target to specific sequence of host genes, while our novel motif does not appear to work in a sequence-specific manner. In this study, siRNAs-m respectively targeting to 4 different viral genes provided a similar potency in protecting animals against the lethal challenge of highly pathogenic H5N1 virus infection. This motif has also been found in many other important viruses, such as SARS-CoV, RSV, AdV, HIV, HBV, and HCV, and thus is likely to provide siRNA-based antiviral agents for not only H5N1 influenza virus but also for other important viral pathogens such as these.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Figure 1:
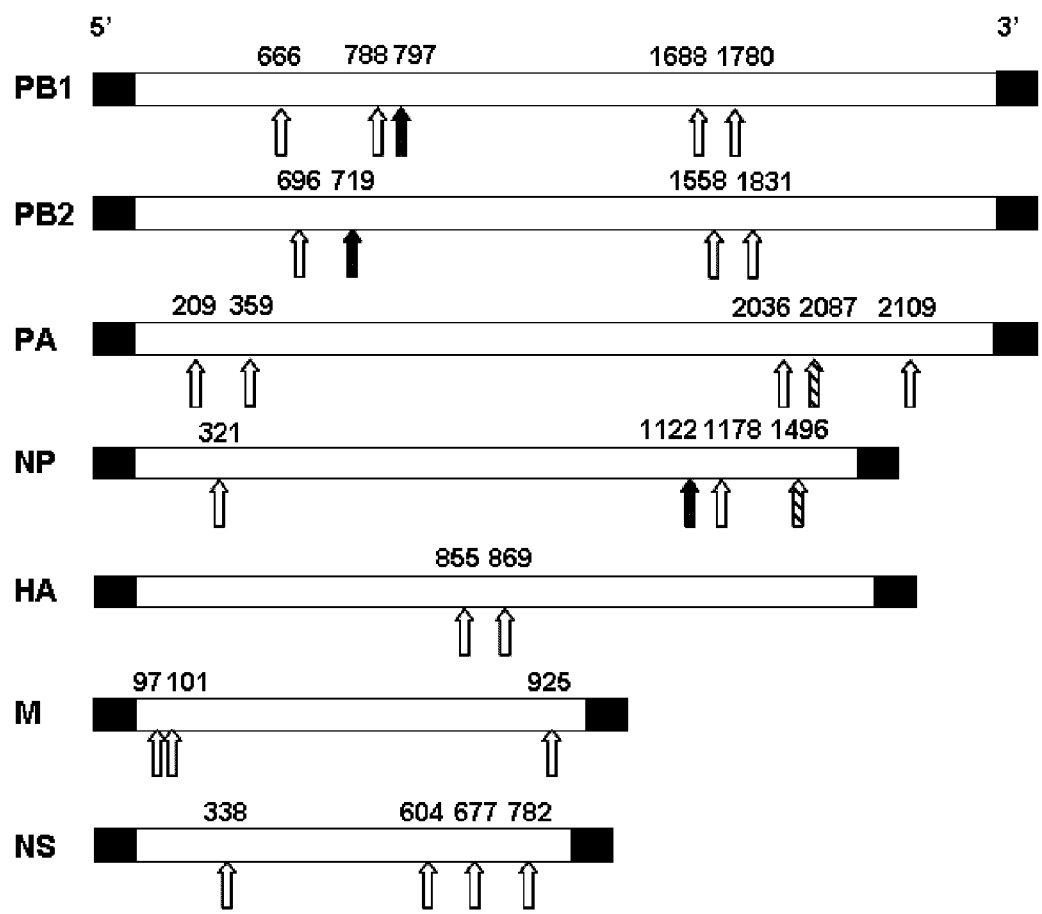
FIG. 1 is a schematic illustration of the locations of siRNA target sequences. Twenty-five siRNAs target the indicated viral genes, including 4 siRNAs-m (black arrows) and 21 siRNAs-n (white arrows). Two reported siRNAs (upward diagonal arrows) are also indicated.
Figure 2A:
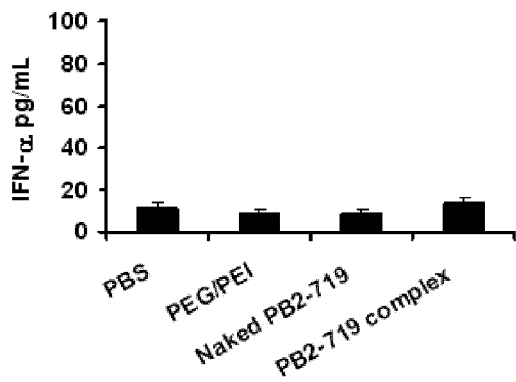
FIG. 2 graphically depicts detection of innate immune responses stimulated by siRNA-m in serum samples. (a) Detection of IFN-α response. (b) Detection of IFN-γ response. (c) Detection of TNF-α response. (d) Detection of IL-6 response. Indicated cytokines in mouse serum samples were detected as described in the legend to FIG. 6.
Figure 2B:
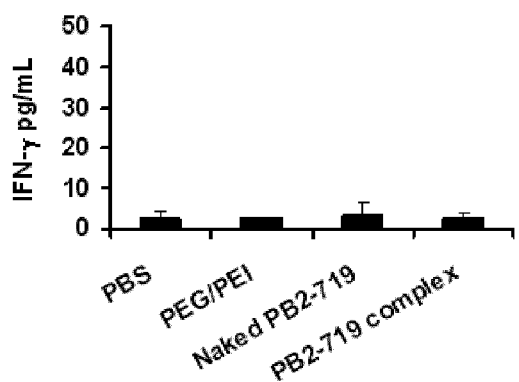
Figure 2C:
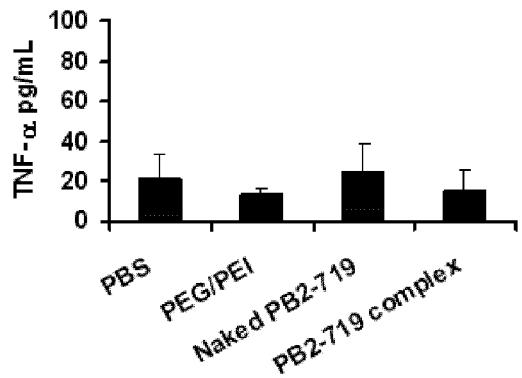
Figure 2D:
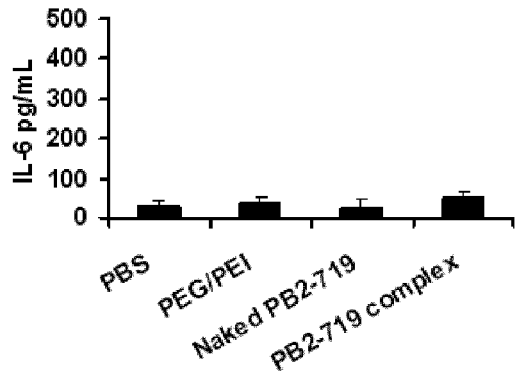

Example 1 siRNAs with the Motif (siRNA-m) Showed Lower Inhibitory Effect than siRNAs without the Motif (siRNA-n) in Cultured Cells Twenty-five siRNA duplexes respectively targeting PB1, PB2, PA, NP, M, NS and HA genes of influenza A virus, including 4 siRNAs that contain a novel motif (designated siRNAs-m) and 21 siRNAs that do not contain the motif (designated siRNAs-n), were designed and synthesized (FIG. 1 and Table 1).

TABLE 1

Sequences of siRNAs designed and tested in this study

| Name# | Forward sequence (5'-3') | |
|---|---|---|
| PB1-666 | GACACUGAACACAAUGACAdTdT | SEQ ID NO: 1 |
| PB1-788 | GUGAGAAACUUGAGCAAUCdTdT | SEQ ID NO: 2 |
| PB1-797 | UUGAGCAAUCUGGACUCCdTdT | SEQ ID NO: 3 |
| PB1-1688 | GAGGGGAUACGCAAAUCCAdTdT | SEQ ID NO: 4 |
| PB1-1780 | GGAGGACCAAAUCUAUACAdTdT | SEQ ID NO: 5 |
| PB2-696 | GCAUUUGACUCAAGGGACCdTdT | SEQ ID NO: 6 |
| PB2-719 | GGGAACAGAUGUACACUCCdTdT | SEQ ID NO: 7 |
| PB2-1558 | GAAACCCAGGGAACAGAGAdTdT | SEQ ID NO: 8 |
| PB2-1831 | GAUACUGUCCAGAUAAUAAdTdT | SEQ ID NO: 9 |
| PA-209 | GAAACACCGAUUUGAAAUAdTdT | SEQ ID NO: 10 |
| PA-359 | GACACGGAGGGAAGUUCAUdTdT | SEQ ID NO: 11 |
| PA-2036 | GCUUAAUGCGUCUUGGUUCdTdT | SEQ ID NO: 12 |
| PA-2087 | GCAAUUGAGGAGUGCCUGAdTdT | SEQ ID NO: 13 |
| PA-2109 | GGUUCAACUCCUUCCUCGCdTdT | SEQ ID NO: 14 |
| NP-321 | GCUAAUUCUGUACGACAAAdTdT | SEQ ID NO: 15 |
| NP-1122 | GGACUCCAACACUCUUGAAdTdT | SEQ ID NO: 16 |
| NP-1178 | GAGGAAACACCAACCAGCAdTdT | SEQ ID NO: 17 |

TABLE 1-continued

Sequences of siRNAs designed and tested in this study

| Name[#] | Forward sequence (5'-3') | |
|---|---|---|
| NP-1496 | GGAUCUUAUUUCUUCGGAGdTdT | SEQ ID NO: 18 |
| HA-869 | GCAACACCAAGUGUCAAACdTdT | SEQ ID NO: 19 |
| HA-855 | GGAAUAUGGUAACUGCAACdTdT | SEQ ID NO: 20 |
| M-97 | GCAGGAAAGAACACCGAUCdTdT | SEQ ID NO: 21 |
| M-101 | GAAAGAACACCGAUCUCGAdTdT | SEQ ID NO: 22 |
| M-925 | ACAGCAGAGUGCUGUGGAUdTdT | SEQ ID NO: 23 |
| NS-338 | AAAUGGACCAGGCAAUAAUdTdT | SEQ ID NO: 24 |
| NS-604 | GAUGAGGAUGGGAGACUUCdTdT | SEQ ID NO: 25 |
| NS-677 | GAAGAAAUAAGGUGGCUGAdTdT | SEQ ID NO: 26 |
| NS-782 | GUGGAGCAAGAGAUAAGAGdTdT | SEQ ID NO: 27 |

Antiviral effects of these siRNAs against H5N1 influenza A virus strain A/Vietnam/1194/04 was evaluated in cultured MDCK cells. Two reported siRNAs, PA-2087 and NP-1496[8,9], were included in the experiment as positive controls. In addition to these two positive control siRNAs, ten of 25 newly designed siRNAs could significantly suppress viral replication in cell culture. An inhibition of more than 75% over the untreated control was observed (FIG. 3a). Among the siRNAs tested, all 4 siRNAs-m (100%) but only 6 of 21 siRNA-n (28.6%) were effective. However, the antiviral effect of siRNAs-m, except for PA-2109, was 10- to 1000-fold lower than that of siRNAs-n targeting the same viral gene (FIG. 3a), indicating that siRNAs-m basically exhibited lower antiviral effect than similar siRNAs-n as evaluated in the cell culture system.

Although siRNAs-m showed lower antiviral effect in cultured cells, we thought that the in vivo situation might be different. Therefore, we selected four pairs of siRNAs-m and siRNAs-n targeting viral genes PB1, PB2, PA and NP, respectively, for further study in mice infected with a highly virulent H5N1 virus strain A/Vietnam/1194/04. The target sequences of these paired siRNAs are very close in viral genome (FIG. 3b). Two siRNAs-n PA-2087 and NP-1496 were included because they were reported to be effective siRNAs showing fairly good anti-H5N1 activity in cultured cells and in vivo[8, 9].

Example 2 siRNAs-m Showed More Pronounced Prophylactic and Therapeutic Effects than siRNAs-n in Animal Models To evaluate prophylactic effect, the mice were given intratracheally (i.t.) one dose (100, 50 or 25 µg/dose) of the siRNAs 16-18 hours before the viral challenge (Table 2). The results showed that all mice treated with siRNAs-m (PB 1-797, PB2-719, PA-2109 and NP-1122) survived (survival rate=100%) (FIGS. 4a, b, c, and d). In contrast, siRNAs-n showed much lower protective effect in the mouse model. The survival rates of mice treated with 100 µg/dose of PB1-788 (FIG. 4a) and NP-1496 (FIG. 4d) were 30% and 10%, respectively, but dropped to 0% when the mice were given 50 or 25 µg/dose of the siRNAs. Notably, sequences of siRNA-m PB1-797 and siRNA-n PB1-788 are overlapped for 10 nucleotides (nt). All mice died (survival rate=0%) when they were treated with either PB2-696 (FIG. 4b) or PA-2087 (FIG. 4c), although their survival days were 1-2 days longer than the untreated mice. Consistently, the body weight of the mice treated by siRNAs-m maintained at similar levels during the 14-day observation period, whereas that of mice treated with the siRNAs-n declined from the 6th day post-challenge (FIG. 4e-h) and showed signs of sickness. The results indicated that siRNAs-m could provide a potent prophylactic effect against a highly virulent strain of H5N1 virus, which was much more pronounced than that of the siRNAs-n (P<0.01-0.03), including two effective siRNAs reported previously by others[8,9].

TABLE 2

Treatment regimens for evaluation of prophylactic and therapeutic antiviral effects of siRNAs-m and siRNAs-n in mouse model

| siRNAs-m | |
|---|---|
| | Number |
| Prophylactic regimen | |
| PB1-797 100 µg × 1 dose | 13* |
| PB1-797 50 µg × 1 dose | 5 |
| PB1-797 25 µg × 1 dose | 5 |
| PB2-719 100 µg × 1 dose | 13* |
| PB2-719 50 µg × 1 dose | 5 |
| PB2-719 25 µg × 1 dose | 5 |
| NP-1122 100 µg × 1 dose | 13* |
| NP-1122 50 µg × 1 dose | 5 |
| NP-1122 25 µg × 1 dose | 5 |
| PA-2109 100 µg × 1 dose | 13* |
| PA-2109 50 µg × 1 dose | 5 |
| PA-2109 25 µg × 1 dose | 15[#] |
| PEG/PEI 30 µl × 1 dose | 13* |
| PB2-1291 100 µg × 1 dose | 5 |
| Therapeutic regimens | |
| NP-1122 100 µg × 4 doses | 10 |
| PEG/PEI 30 µl × 4 doses | 10 |

| siRNAs-n | |
|---|---|
| | Number |
| Prophylactic regimen | |
| PB1-788 100 µg × 1 dose | 13* |
| PB1-788 50 µg × 1 dose | 5 |
| PB1-788 25 µg × 1 dose | 5 |
| PB2-696 100 µg × 1 dose | 13* |
| PB2-696 50 µg × 1 dose | 5 |
| PB2-696 25 µg × 1 dose | 5 |
| NP-1496 100 µg × 1 dose | 13* |
| NP-1496 50 µg × 1 dose | 5 |
| NP-1496 25 µg × 1 dose | 5 |
| PA-2087 100 µg × 1 dose | 13* |
| PA-2087 50 µg × 1 dose | 5 |
| PA-2087 25 µg × 1 dose | 5 |
| PBS 30 µl × 1 dose | 23* |
| Therapeutic regimens | |
| NP-1496 100 µg × 4 doses | 10 |
| PBS 30 µl × 4 doses | 10 |

To assess therapeutic effects of the siRNAs, the mice were intranasally (i.n.) administered 100 µg/dose·4 dosing of siRNA-m NP-1122 and siRNA-n NP-1496 at 24 hours interval. The treatment was started at 24 hours post-challenge (Table 2). As shown in FIG. 4i, the survival rate of the mice treated with siRNA-m (NP-1122) was 60%, which was significantly higher than that of mice treated with siRNA-n (NP-1496) (0%) (P<0.02). Consistent with this, the body weight loss of the former was lesser than that of the later (FIG. 4j).

These results have demonstrated that siRNAs-m provides considerable therapeutic effect in an animal model whereas siRNAs-n does not.

Example 3 siRNAs-m Potently Suppressed Viral Replication and Tissue Damage in Lungs

To further compare the inhibition of viral replication and suppression of tissue damage in lungs between mice treated with siRNAs-m and siRNAs-n, the animals receiving prophylactic treatment were sacrificed at the 6th day post-challenge and their lungs were collected for detections of viral replication and pathological changes. The virus titers tested by $TCID_{50}$ were undetectable in lung tissues from mice treated with siRNAs-m, while the virus titers in mice treated with siRNAs-n were similar to or even higher than that of the untreated controls (FIG. 5a). Consistently, viral RNA copies measured by real-time RT-PCR were about 50- to 100-fold lower in the lung tissues obtained from mice treated with siRNAs-m than from mice treated with siRNAs-n (FIG. 3b). Histopathological examination of the lung samples further revealed that lung sections from mice treated with siRNAs-m did not show obvious pathological changes, which was similar to the lung section from uninfected mice (normal), whereas lung sections from the mice treated with siRNA-n and from untreated mice (control) showed alveolar damage and interstitial inflammatory infiltration (FIG. 5c). These results have further confirmed that siRNAs-m provides much stronger suppression of virus replication and pathological damage in the mouse lungs than siRNAs-n.

Example 4

Importance of the Motif to In Vivo Antiviral Activity

Figure 6E:
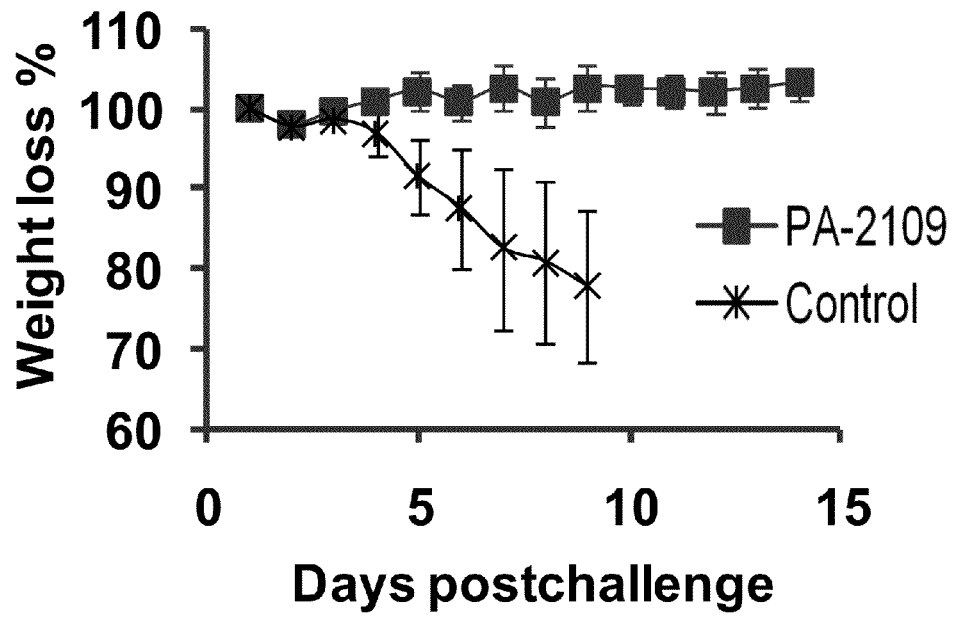
Figure 6F:
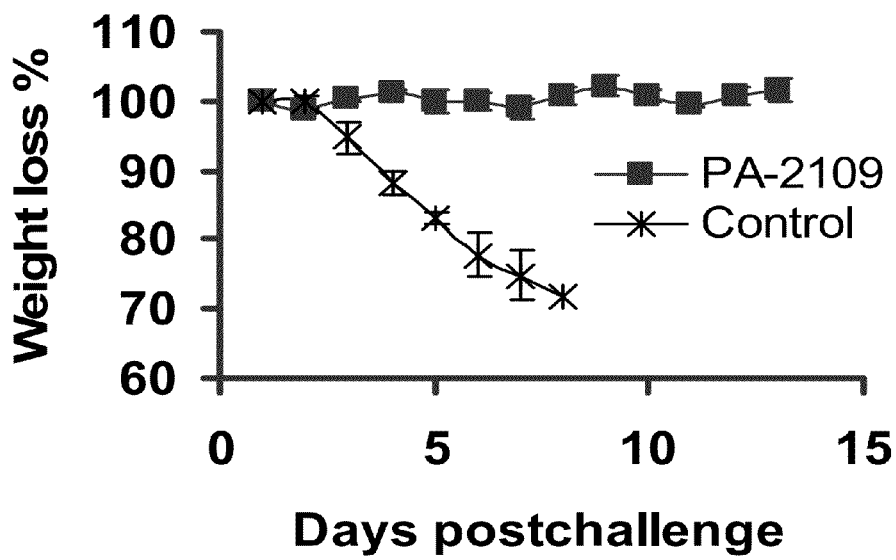
Figure 6G:
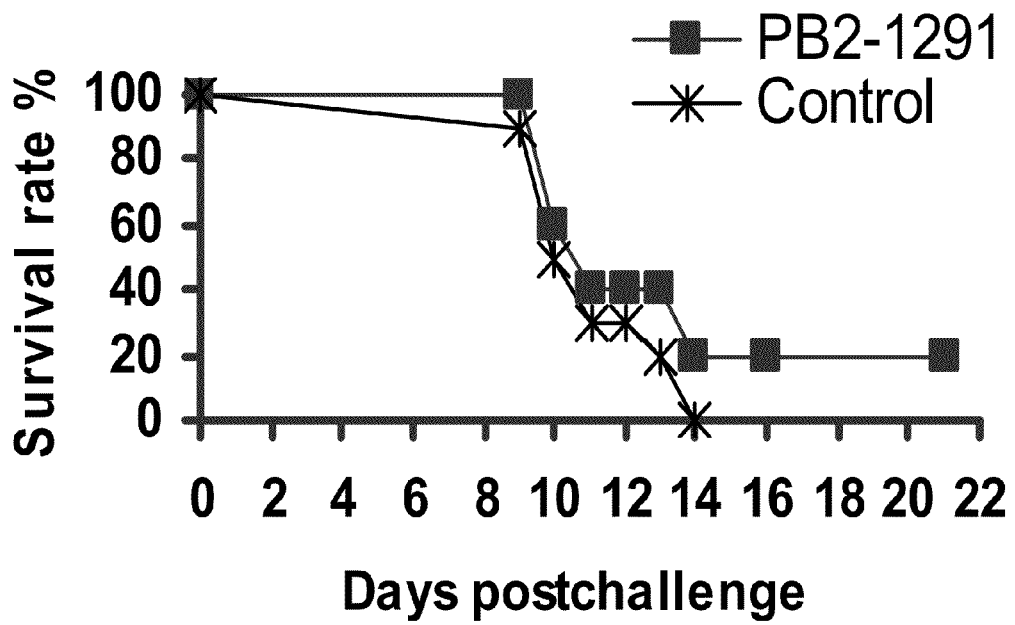
Figure 6H:
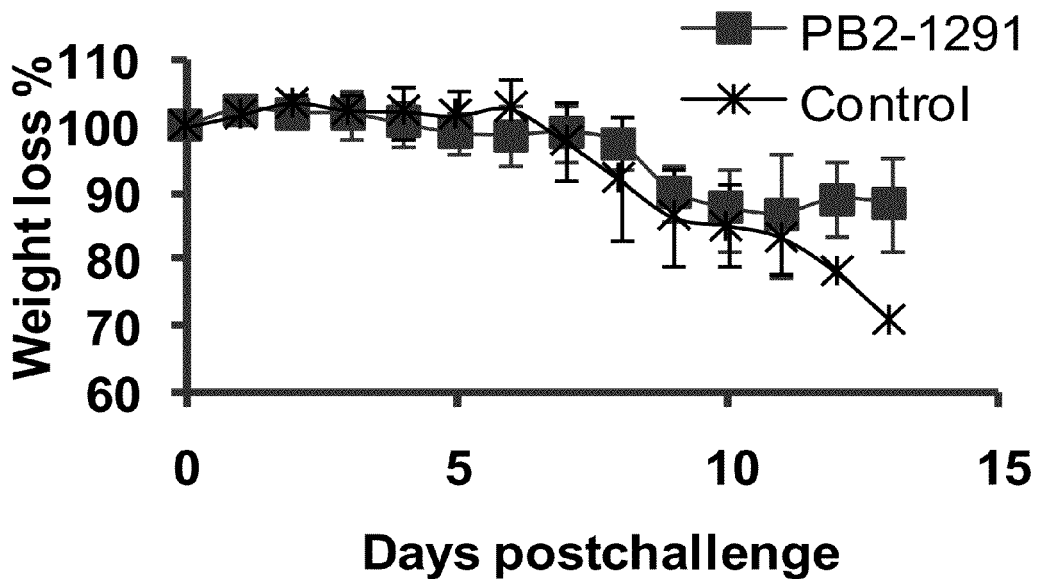

The above results that siRNAs-m showed much lower antiviral effect in cultured cells but displayed higher activity in vivo, indicated that the motif might play an important role in the in vivo antiviral effect of siRNAs-m. To confirm this, we selected a siRNA-m, PA-2109, which has one nt mismatched with two H5N1 virus strains A/Shen Zhen/406H and A/Hong Kong/156/97 (FIG. 6a), for further study. No significant antiviral effect of PA-2109 against these two imperfectly matched virus strains was detected in cultured cells (FIG. 6B). The results showed that the antiviral effect against the imperfectly matched virus strains was at least 8-fold lower than that against the perfectly matched virus strain A/Vietnam/1194/04 (FIG. 7b). In vivo antiviral effect of PA-2109 against the imperfectly matched virus strains was further assessed in mice given 1 dose of 25 μg of PA-2109 prophylactic treatment (Table 2), and then challenged with these two imperfectly matched virus strains, respectively. As shown in FIGS. 6c & d, similar to its antiviral effect against the perfectly matched virus strain observed in prophylactic treatment (FIGS. 4e & f), all treated mice survived (survival rate=100%) and their body weight maintained at similar levels during the 2-week observation period, indicating that the siRNA-m could protect mice from lethal challenge of the imperfectly matched H5N1 virus strains to a similar extent. We further tested in cultured cells and in vivo the antiviral activity of a small RNA duplex, PB2-1291, which targets PB2 gene of the virus. PB2-1291 contains the motif but is a sub-optimal siRNA according to the generally accepted criteria. PB2-1291 did not show any antiviral activity in cell culture (data not shown), but the survival rate of mice was 20%, accompanying with increased survival of 2 days (FIG. 6e). Consistently, the body weight loss of the treated mice occurred 2 days later than that of the untreated control mice, and the body weight of the survived mice increased after 12 days post-challenge (FIG. 6e). Although the in vivo antiviral effect of PB2-1291 was not as good as that of siRNAs-m, it was still more pronounced than most tested siRNAs-n, i.e. PB2-696, PA-2087 and NP-1496. These results further confirmed that the unique motif plays an important role in inducing the potent in vivo antiviral effect of siRNAs-m.

Example 5

The siRNAs-m Stimulated IL-6 Production in Mouse Lungs

Figure 7H:
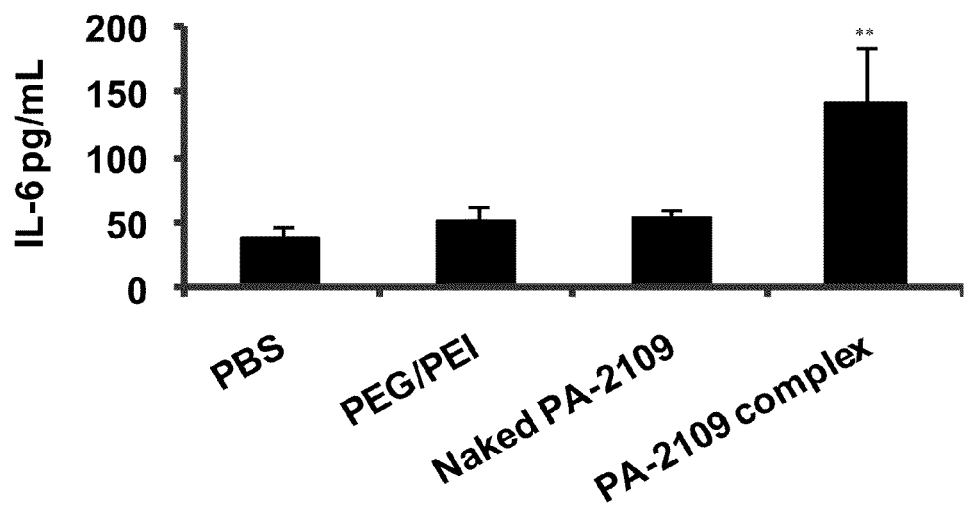

Since it has been reported that siRNAs may stimulate in vivo unanticipated nonspecific effects, such as innate immune responses$_{(14-16)}$, IFN-α, IFN-γ, TNF-α and IL-6, which are important indicators of innate immune responses, were measured in serum samples and lung homogenates collected from mice at different time-points (Table 3). The levels of IFN-α, IFN-γ, TNF-α and IL-6 did not increase in serum samples collected respectively at 7, 15, 24 and 48 h post-treatment (FIG. 2). The levels of IFN-α, IFN-γ and TNF-α were also undetectable in lung homogenates from treated mice (FIGS. 7a, b & c). Interestingly, a high level of IL-6 was detected in the lung homogenate from mice receiving encapsulated siRNA-m PB2-719 (complex) but was not found in the samples from mice given naked PB2-719, encapsulated siRNA-n PB2-696, delivery polymers, or PBS (FIG. 7d). The IL-6 level increased at 3 hours, peaked at 7 hours, and then dropped to low level 10 hours post-treatment (FIG. 7e). A dose-dependent effect was also observed (FIG. 7f). Furthermore, it was demonstrated that the antisense strand but not the sense strand of the siRNA-m was responsible for the stimulation of IL-6 production (FIG. 7g). An alternative siRNA-m targeting another viral gene, PA-2109, was selected to repeat the experiment. The result showed that encapsulated siRNA PA-2109 induced a similar level of IL-6 at 7 hours post-treatment (FIG. 7h), indicating that the production of IL-6 in lungs was indeed induced by the motif but not a specific sequence of PB2-719. Taken together, the siRNAs-m are unlikely to induce a strong innate immune response, but they stimulate an early production of IL-6 in mice.

Example 6

The siRNAs-m Stimulated Strong β-Defensin-4 Generation in Mouse Lungs

Lung tissues were collected from mice treated with siRNAs-m and siRNAs-n at 6 h post-treatment, then tested for mRNAs productions using the 430 2.0 array GeneChip (Affymetrix, Inc, Santa Clara, Calif.) and analyzed using Gene-Spring 10 Software (Agilent Technologies), MA algorithms and gene ontology annotation. The results showed that β-defensin-4 and IL-6 productions stimulated by siRNA-m were about 29-fold and 14-fold higher than that induced by siRNA-n, respectively. The result was further confirmed by detection of mRNA production using real-time RT-PCR. High level of β-denfensin-4 mRNA was detected in the lung homogenate from mice receiving encapsulated siRNAs-m (PB2-719 and PA-2109), but was not found in the samples from mice receiving encapsulated siRNAs-n (PB2-696 and PA-2087), delivery polymers (PEG/PEI), or PBS (FIG. 8a). Similar to the stimulation of IL-6, the antisense strand, not the sense strand of the siRNA-m, was responsible for the stimulation of β-denfensin-4 production (FIG. 8b). The β-denfensin-4 level increased at 3 hours, peaked at 7 hours, and then dropped to low level at 24 hours post-treatment (FIG. 8c). The results also demonstrated that β-denfensin-4 production is dose-dependent (FIG. 8d). Furthermore, it was demonstrated that siRNAs-m stimulated epithelial cells on tracheal membrane to generate much higher level of β-denfensin-4 than siRNAs-n (FIG. 8e). These results demonstrated that siRNAs-m could stimulate an early production of β-denfensin-4 in mice in both mRNA and protein levels.

Example 7

β-Defensin-4 Induced by siRNAs-m Showed Strong Activity Against Ex Vivo and In Vivo H5N1 Viral Infections To test whether the siRNAs-m induced β-denfensin-4 plays an important role against H5N1 virus infection, we cloned and expressed β-denfensin-4 using an *E. coli* system after optimization of the gene. After purification, the expressed β-denfensin-4 showed strong anti-H5N1 virus infection in MDCK cell cultures, reaching a level of $IC_{50}$ at about 45 ng/ml (FIG. 9a). The anti-H5N1 activity of β-denfensin-4 was further evaluated in animal models. The result showed that the treatment with only one dose of 75 μg β-denfensin-4 could protect 40% mice from lethal challenge of H5N1 virus. Even for those mice that are treated with β-denfensin-4 but fail to survive, they are able to live about 2 days longer than controls (FIG. 9b). These ex vivo and in vivo results demonstrated that β-denfensin-4 induced by siRNAs-m indeed have strong anti-H5N1 activity.

Example 8

Materials and Methods

Cell Culture and Viruses.

Madin-Darby canine kidney (MDCK) cells were maintained in minimum essential medium (MEM) (GIBCO BRL) supplemented with 10% fetal-calf serum (FCS) and 1% penicillin and streptomycin (P/S) at 37° C. in 5% $CO_2$. Aliquots of stocks of influenza A virus strains A/Vietnam/1194/2004, A/Shen Zhen/406H and A/Hong Kong/156/97 were grown in embryonated chicken eggs at 37° C. Virus-containing allantoic fluid was harvested 48 h after virus inoculation and stored at −80° C. Virus titer was measured by hemagglutination assay and $TCID_{50}$. The 50% lethal dose ($LD_{50}$) was determined in mice after serial dilution of the stock. All experiments involving H5N1 viruses were performed in the biosafety level 3 facility of the Department of Microbiology at the University of Hong Kong.

Preparation of siRNAs.

The siRNAs were designed to respectively target PB1, PB2, PA, NP, M, NS and HA genes of H5N1 influenza A virus (FIG. 1 & Table 1) using siRNA target designer program from Promega. BLAST results confirmed that none of the targeted regions share homology with human and mouse genomes. All siRNAs used in this study were chemically synthesized and supplied as desalted, pre-annealed or annealed duplexes (Invitrogen or Qiagen, USA).

Evaluation of Antiviral Effect in Cultured Cells.

siRNAs were transfected into MDCK cells in 24-well plates using LIPOFECTAMINE™ RNAiMAX (Invitrogen, USA) according to the instructions of the supplier. The transfected cells were infected with 100 $TCID_{50}$ virus per well 16-18 h after the transfection. Supernatants were collected at 48 h to detect viral load by $TCID_{50}$ and real time RT-PCR as described previously$_{(17,31)}$.

Preparation of PEG8-PEI1.8.

Methoxy N-hydroxysuccinimide polyethylene glycol (mPEG-NHS) was prepared as described previously$_{(32)}$. PEG8-PEI1.8 was synthesized by adding 1 g of hyperbranched PEI (1.8 kDa, Aldrich) and 8.8 g of mPEG-NHS to phosphate buffered saline (PBS, pH 7.4) and the solution was magnetically stirred at room temperature overnight. The resulting solution was purified by membrane dialysis (MW cutoff: 3.5 kDa) in distilled water for 48 h, and then lyophilized to obtain white powder. PEG grafting density of PEI was 8 as characterized by $_1$H NMR (Varian 300-MHz NMR spectrometer, CA, USA) in deuterated chloroform.

Evaluation of In Vivo Antiviral Effect.

BALB/c female mice, 6-8 weeks old, were kept in biosafety level 3 housing and given access to standard pellet feed and water ad libitum. All experimental protocols followed the standard operating procedures of the approved biosafety level 3 animal facilities and were approved by the Animal Ethics Committee. The siRNAs were encapsulated into PEG8-PEI1.8 at the Nitrogen/Phosphorus weight ratio of 7. The mixture was vortexed for 20 sec and then incubated at room temperature for 30 min. The mice were i.t. given 1 dose of the siRNA mixture for prophylactics or i.n. 4 doses of the siRNAs for therapy and i.n. inoculated with 10 $LD_{50}$ of the virus (Table 2). Control mice were given PBS and/or PEG8-PEI1.8. Survival, body weight and general conditions were monitored for 21 days or until death. For virological and pathological tests, mice were sacrificed six days after the challenge. Blood, lung, spleen and brain samples were collected.

Analysis of Innate Immune Responses.

The mice were i.t. given naked and/or encapsulated siRNAs-m, siRNA-n, PEGS-PEI1.8 and PBS (Supplementary Table 3). Blood and lung samples were collected from the mice sacrificed at different time-points. IFN-α, IFN-γ, TNF-α and IL-6 in serum samples and lung homogenates were tested by ELISA assay.

Statistical Analysis.

Statistical analysis of survival time and rate was performed by the log rank Kaplan-Meier and chi square tests, respectively. In other cases, statistics was calculated by the paired two-tailed Student's t test using Stata statistical software. Results were considered significant at $P \leq 0.05$.

Accession Numbers.

GeneBank accession numbers for A/Vietnam/1194/04, A/Hong Kong/156/97 and A/Shenzhen/406H H5N1 virus sequences are AY651498, AF036359 and EF137709 for NP, AY651610, AF036361 and EF137711 for PA, AY651664, AF036362 and EF137712 for PB1, AY651718, AF036363 and EF137713 for PB2, respectively.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Horimoto, T. & Kawaoka, Y. Influenza: lessons from past pandemics, warnings from current incidents. *Nat Rev Microbiol* 3, 591-600 (2005).

2. Yuen, K. Y., et al. Clinical features and rapid viral diagnosis of human disease associated with avian influenza A H5N1 virus. *Lancet* 351, 467-471 (1998).
3. Beigel, J. H., et al. Avian influenza A (H5N1) infection in humans. *The New England journal of medicine* 353, 1374-1385 (2005).
4. Castle, S. C. Clinical relevance of age-related immune dysfunction. *Clin Infect Dis* 31, 578-585 (2000).
5. Luscher-Mattli, M. Influenza chemotherapy: a review of the present state of art and of new drugs in development. *Archives of virology* 145, 2233-2248 (2000).
6. Elbashir, S. M., et al. Duplexes of 21-nucleotide RNAs mediate RNA interference in cultured mammalian cells. *Nature* 411, 494-498 (2001).
7. Fire, A., et al. Potent and specific genetic interference by double-stranded RNA in *Caenorhabditis elegans*. *Nature* 391, 806-811 (1998).
8. Ge, Q., et al. Inhibition of influenza virus production in virus-infected mice by RNA interference. *Proceedings of the National Academy of Sciences of the United States of America* 101, 8676-8681 (2004).
9. Tompkins, S. M., Lo, C. Y., Tumpey, T. M. & Epstein, S. L. Protection against lethal influenza virus challenge by RNA interference in vivo. *Proceedings of the National Academy of Sciences of the United States of America* 101, 8682-8686 (2004).
10. Ge, Q., et al. RNA interference of influenza virus production by directly targeting mRNA for degradation and indirectly inhibiting all viral RNA transcription. *Proceedings of the National Academy of Sciences of the United States of America* 100, 2718-2723 (2003).
11. Zhou, H., et al. Effective small interfering RNAs targeting matrix and nucleocapsid protein gene inhibit influenza A virus replication in cells and mice. *Antiviral Research* (2007).
12. Hui, E. K., Yap, E. M., An, D. S., Chen, I. S. & Nayak, D. P. Inhibition of influenza virus matrix (M1) protein expression and virus replication by U6 promoter-driven and lentivirus-mediated delivery of siRNA. *J Gen Virol* 85, 1877-1884 (2004).
13. McCown, M., Diamond, M. S. & Pekosz, A. The utility of siRNA transcripts produced by RNA polymerase i in down regulating viral gene expression and replication of negative- and positive-strand RNA viruses. *Virology* 313, 514-524 (2003).
14. Marques, J. T. & Williams, B. R. G. Activation of the mammalian immune system by siRNAs. *Nat Biotech* 23, 1399-1405 (2005).
15. Judge, A. D., et al. Sequence-dependent stimulation of the mammalian innate immune response by synthetic siRNA. *Nature biotechnology* 23, 457-462 (2005).
16. Hornung, V., et al. Sequence-specific potent induction of IFN-alpha by short interfering RNA in plasmacytoid dendritic cells through TLR7. *Nature medicine* 11, 263-270 (2005).
17. Zheng, B. J., et al. Delayed antiviral plus immunomodulator treatment still reduces mortality in mice infected by high inoculum of influenza A/H5N1 virus. *Proceedings of the National Academy of Sciences of the United States of America* 105, 8091-8096 (2008).
18. Bitko, V., Musiyenko, A., Shulyayeva, 0. & Barik, S Inhibition of respiratory viruses by nasally administered siRNA. *Nature medicine* 11, 50-55 (2005).
19. Li, B.-j., et al. Using siRNA in prophylactic and therapeutic regimens against SARS coronavirus in *Rhesus macaque*. *Nature medicine* 11, 944-951 (2005).
20. Schlee, M., Hornung, V. & Hartmann, G. siRNA and is RNA: Two Edges of One Sword. *Mol Ther* 14, 463-470 (2006).
21. Sioud, M. Induction of inflammatory cytokines and interferon responses by double-stranded and single-stranded siRNAs is sequence-dependent and requires endosomal localization. *Journal of molecular biology* 348, 1079-1090 (2005).
22. Imai, Y., et al. Identification of oxidative stress and Toll-like receptor 4 signaling as a key pathway of acute lung injury. *Cell* 133, 235-249 (2008).
23. Salomon, R., Hoffmann, E. & Webster, R. G. Inhibition of the cytokine response does not protect against lethal H5N1 influenza infection. *Proceedings of the National Academy of Sciences of the United States of America* 104, 12479-12481 (2007).
24. Bals, R. & Hiemstra, P. S. Innate immunity in the lung: how epithelial cells fight against respiratory pathogens. *Eur Respir J* 23, 327-333 (2004).
25. Nadeau, W. J., Pistole, T. G. & McCormick, B. A. Polymorphonuclear leukocyte migration across model intestinal epithelia enhances *Salmonella typhimurium* killing via the epithelial derived cytokine, IL-6. *Microbes and infection/Institut Pasteur* 4, 1379-1387 (2002).
26. Meusel, T. R. & Imani, F. Viral induction of inflammatory cytokines in human epithelial cells follows a p38 mitogen-activated protein kinase-dependent but NF-kappa B-independent pathway. *J Immunol* 171, 3768-3774 (2003).
27. Monick, M. M., et al. Respiratory syncytial virus up-regulates TLR4 and sensitizes airway epithelial cells to endotoxin. *The Journal of biological chemistry* 278, 53035-53044 (2003).
28. Wick, M. J., Madara, J. L., Fields, B. N. & Normark, S. J. Molecular cross talk between epithelial cells and pathogenic microorganisms. *Cell* 67, 651-659 (1991).
29. Diamond, G., Legarda, D. & Ryan, L. K. The innate immune response of the respiratory epithelium. *Immunological reviews* 173, 27-38 (2000).
30. Dentener, M. A., et al. Production of the acute-phase protein lipopolysaccharide-binding protein by respiratory type II epithelial cells: implications for local defense to bacterial endotoxins. *American journal of respiratory cell and molecular biology* 23, 146-153 (2000).
31. Wang, M., et al. Food markets with live birds as source of avian influenza. *Emerging infectious diseases* 12, 1773-1775 (2006).
32. Shuai, X., Merdan, T., Unger, F., Wittmar, M. & Kissel, T. Novel Biodegradable Ternary Copolymers hy-PEI-g-PCL-b-PEG: Synthesis, Characterization, and Potential as Efficient Nonviral Gene Delivery Vectors. *Macromolecules* 36, 5751-5759 (2003).
33. Sun, L., et al., Human beta-defensins suppress human immunodeficiency virus infection: potential role in mucosal protection. J Virol, 2005. 79(22):14318-29.
34. Klotman M E and Chang T L. Defensins in innate antiviral immunity. Nat Rev Immunol, 2006. 6(6):447-56.
35. Biragyn A, et al. Toll-like receptor 4-dependent activation of dendritic cells by beta-defensin 2. Science, 2002. 298 (5595):1025-9.
36. Becker M N, et al. CD14-dependent lipopolysaccharide-induced beta-defensin-2 expression in human tracheobronchial epithelium. J Biol Chem, 2000. 275(38):29731-6.
37. Rivas-Santiago B, et al. beta-Defensin gene expression during the course of experimental tuberculosis infection. J Infect Dis, 2006. 194(5):697-701.

38. Chong K T, Thangavel R R, Tang X. Enhanced expression of murine beta-defensins (MBD-1, -2, -3, and -4) in upper and lower airway mucosa of influenza virus infected mice. Virology, 2008. 380(1):136-43.

We claim:

1. A method of stimulating β-defensin or IL-6 production in a subject comprising administering to the subject an effective amount of a nucleic acid molecule, wherein said nucleic acid molecule is an siRNA comprising an antiviral functional motif selected from the motif GGAGU or the reverse motif ACUCC, wherein said siRNA comprises a sequence selected from SEQ ID NO: 3, SEQ ID NO: 7, SEQ ID NO: 14, SEQ ID NO: 16, SEQ ID NO: 28, SEQ ID NO: 30, SEQ ID NO: 32, SEQ ID NO: 34, SEQ ID NO: 36, and SEQ ID NO: 37.

2. A method of stimulating β-defensin or IL-6 production in a subject comprising administering to the subject an effective amount of a composition, wherein said composition comprises an siRNA that comprises an antiviral functional motif selected from the motif GGAGU or the reverse motif ACUCC, and a pharmaceutically acceptable carrier, wherein said siRNA comprises a sequence selected from SEQ ID NO: 3, SEQ ID NO: 7, SEQ ID NO: 14, SEQ ID NO: 16, SEQ ID NO: 28, SEQ ID NO: 30, SEQ ID NO: 32, SEQ ID NO: 34, SEQ ID NO: 36, and SEQ ID NO: 37.

3. The method according to claim 1, wherein IL-6 production is stimulated.

4. The method according to claim 2, wherein IL-6 production is stimulated.

5. The method according to claim 1, wherein β-defensin production is stimulated.

6. The method according to claim 2, wherein β-defensin production is stimulated.

7. A method of stimulating β-defensin or IL-6 production in a subject comprising administering to the subject an effective amount of a nucleic acid molecule, wherein said nucleic acid molecule comprises an antiviral functional motif selected from the motif GGAGU or the reverse motif ACUCC, wherein said nucleic acid comprises a sequence selected from SEQ ID NO: 3, SEQ ID NO: 7, SEQ ID NO: 14, SEQ ID NO: 16, SEQ ID NO: 28, SEQ ID NO: 30, SEQ ID NO: 32, SEQ ID NO: 34, SEQ ID NO: 36, and SEQ ID NO: 37.

8. The method according to claim 7, wherein β-defensin production is stimulated.

9. A method of stimulating β-defensin or IL-6 production in a subject comprising administering to the subject an effective amount of a composition, wherein said composition comprises a nucleic acid molecule that comprises an antiviral functional motif selected from the motif GGAGU or the reverse motif ACUCC, and a pharmaceutically acceptable carrier, wherein said nucleic acid molecule comprises a sequence selected from SEQ ID NO: 3, SEQ ID NO: 7, SEQ ID NO: 14, SEQ ID NO: 16, SEQ ID NO: 28, SEQ ID NO: 30, SEQ ID NO: 32, SEQ ID NO: 34, SEQ ID NO: 36, and SEQ ID NO: 37.

10. The method according to claim 9, wherein β-defensin production is stimulated.

* * * * *

UNITED STATES PATENT AND TRADEMARK OFFICE
CERTIFICATE OF CORRECTION

Page 1 of 1

PATENT NO. : 8,828,962 B2
APPLICATION NO. : 13/323364
DATED : September 9, 2014
INVENTOR(S) : Bojian Zheng, Hongyan Sui and Yongping Lin It is certified that error appears in the above-identified patent and that said Letters Patent is hereby corrected as shown below:

In the specification,

Column 2,
Line 24, "and (d)" should read --and (d).--.
Line 30, "PEGS" should read --PEG8--.
Line 32, "and (j)" should read --and (j).--.
Line 37, "PEGS" should read --PEG8--.
Line 39, "or unstill" should read --or until--.
Line 44, "PEGS" should read --PEG8--.

Column 31,
Line 25, "45 ng/ml" should read --45 µg/ml--.

Column 32,
Line 33, "PEGS" should read --PEG8--.

Signed and Sealed this
Fourteenth Day of April, 2015

Michelle K. Lee
*Director of the United States Patent and Trademark Office*

```
                        SEQUENCE LISTING

<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 1
gacacugaac acaaugacat t                                              21

<210> SEQ ID NO 2
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 2
gugagaaacu ugagcaauct t                                              21

<210> SEQ ID NO 3
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 3
uugagcaauc uggacuccct t                                              21

<210> SEQ ID NO 4
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 4
gaggggauac gcaaauccat t                                              21

<210> SEQ ID NO 5
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 5
ggaggaccaa aucuauacat t                                              21

<210> SEQ ID NO 6
<211> LENGTH: 21
<212> TYPE: DNA
```

```
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 6
gcauuugacu caagggacct t                                              21

<210> SEQ ID NO 7
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 7
gggaacagau guacacucct t                                              21

<210> SEQ ID NO 8
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 8
gaaacccagg gaacagagat t                                              21

<210> SEQ ID NO 9
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 9
gauacugucc agauaauaat t                                              21

<210> SEQ ID NO 10
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 10
gaaacaccga uuugaaauat t                                              21

<210> SEQ ID NO 11
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 11
gacacggagg gaaguucaut t                                              21
```

```
<210> SEQ ID NO 12
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 12
gcuuaaugcg ucuugguuct t                                              21

<210> SEQ ID NO 13
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 13
gcaauugagg agugccugat t                                              21

<210> SEQ ID NO 14
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 14
gguucaacuc cuuccucgct t                                              21

<210> SEQ ID NO 15
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 15
gcuaauucug uacgacaaat t                                              21

<210> SEQ ID NO 16
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 16
ggacuccaac acucuugaat t                                              21

<210> SEQ ID NO 17
<211> LENGTH: 21
<212> TYPE: DNA
<213> ORGANISM: Artificial Sequence
<220> FEATURE:
<223> OTHER INFORMATION: Sequence is synthesized
<220> FEATURE:
```

-continued

```
<223> OTHER INFORMATION: combined sequence listing DNA/RNA

<400> SEQUENCE: 17
gaggaaacac caaccagcat t                                             21

<210> SEQ ID NO 18
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 18
ggaucuuauu ucuucggagt t                                             21

<210> SEQ ID NO 19
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 19
gcaacaccaa gugucaaact t                                             21

<210> SEQ ID NO 20
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 20
ggaauauggu aacugcaact t                                             21

<210> SEQ ID NO 21
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 21
gcaggaaaga acaccgauct t                                             21

<210> SEQ ID NO 22
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 22
gaaagaacac cgaucucgat t                                             21

<210> SEQ ID NO 23
<211> LENGTH: 21
```

```
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 23
acagcagagu gcuguggaut t                                              21

<210> SEQ ID NO 24
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 24
aaauggacca ggcaauaaut t                                              21

<210> SEQ ID NO 25
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 25
gaugaggaug ggagacuuct t                                              21

<210> SEQ ID NO 26
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 26
gaagaaauaa gguggcugat t                                              21

<210> SEQ ID NO 27
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 27
guggagcaag agauaagagt t                                              21

<210> SEQ ID NO 28
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 28
```

-continued

```
gggaguccag auugcucaat t                                      21

<210> SEQ ID NO 29
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 29
gauugcucaa guuucucact t                                      21

<210> SEQ ID NO 30
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 30
ggaguguaca ucuguuccct t                                      21

<210> SEQ ID NO 31
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 31
ggucccuuga gucaaaugct t                                      21

<210> SEQ ID NO 32
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 32
gcgaggaagg aguugaacct t                                      21

<210> SEQ ID NO 33
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 33
ucaggcacuc cucaauugct t                                      21

<210> SEQ ID NO 34
<211> LENGTH: 21
<212> TYPE: DNA
<213> ORGANISM: Artificial Sequence
<220> FEATURE:
<223> OTHER INFORMATION: Sequence is synthesized
```

```
<220> FEATURE:
<223> OTHER INFORMATION: combined sequence listing DNA/RNA

<400> SEQUENCE: 34
uucaagagug uuggagucct t                                              21

<210> SEQ ID NO 35
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 35
cuccgaagaa auaagauccu t                                              21

<210> SEQ ID NO 36
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 36
augcaucaac uccugagact t                                              21

<210> SEQ ID NO 37
<211> LENGTH: 21
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA

<400> SEQUENCE: 37
gucucaggag uugaugcaut t                                              21

<210> SEQ ID NO 38
<211> LENGTH: 19
<212> TYPE: DNA
<213> ORGANISM: Influenza A virus

<400> SEQUENCE: 38
gguucaacuc cuuccucac                                                 19

<210> SEQ ID NO 39
<211> LENGTH: 19
<212> TYPE: DNA
<213> ORGANISM: Influenza A virus

<400> SEQUENCE: 39
gguucaacuc cuuccucac                                                 19

<210> SEQ ID NO 40
<211> LENGTH: 19
<212> TYPE: DNA
<213> ORGANISM: Artificial Sequence
<220> FEATURE:
<223> OTHER INFORMATION: Sequence is synthesized
<220> FEATURE:
<223> OTHER INFORMATION: combined sequence listing DNA/RNA
```

```
<400> SEQUENCE: 40
gguucaacuc cuuccucgc                                                  19
```